US011583842B2

(12) United States Patent
Yeung et al.

(10) Patent No.: US 11,583,842 B2
(45) Date of Patent: Feb. 21, 2023

(54) ZWITTERIONIC CATALYSTS FOR (TRANS)ESTERIFICATION: APPLICATION IN FLUOROINDOLE-DERIVATIVES AND BIODIESEL SYNTHESIS

(71) Applicant: The Chinese University of Hong Kong, Hong Kong (CN)

(72) Inventors: Ying-Yeung Yeung, Hong Kong (CN); Ying-Pong Lam, Hong Kong (CN); Zhihai Ke, Hong Kong (CN); Xinyan Wang, Guangdong (CN); Fei Tan, Hong Kong (CN); Wing-Hin Ng, Hong Kong (CN); Ying-Lung Steve Tse, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 308 days.

(21) Appl. No.: 16/934,534

(22) Filed: Jul. 21, 2020

(65) Prior Publication Data
US 2021/0023539 A1 Jan. 28, 2021

Related U.S. Application Data

(60) Provisional application No. 62/878,044, filed on Jul. 24, 2019.

(51) Int. Cl.
| B01J 31/02 | (2006.01) |
| B01J 37/04 | (2006.01) |
| C07D 213/90 | (2006.01) |
| C07D 207/09 | (2006.01) |
| C07D 233/61 | (2006.01) |
| C07D 401/04 | (2006.01) |

(52) U.S. Cl.
CPC .......... *B01J 31/0271* (2013.01); *B01J 37/04* (2013.01); *C07D 207/09* (2013.01); *C07D 213/90* (2013.01); *C07D 233/61* (2013.01); *C07D 401/04* (2013.01); *B01J 2231/49* (2013.01); *B01J 2531/002* (2013.01)

(58) Field of Classification Search
None
See application file for complete search history.

(56) References Cited

FOREIGN PATENT DOCUMENTS

| CN | 102532128 A | 7/2012 |
| CN | 104876848 A | 9/2015 |
| CN | 107663165 A | 2/2018 |
| EP | 0121972 A2 * | 3/1984 ............ C07D 211/66 |

OTHER PUBLICATIONS

ACS Catalysis, vol. 9, No. 9, pp. 8083-8092, Jul. 22 (Year: 2019).*
Toda, Y. et al., "A Phosphonium Ylide as an Ionic Nucleophilic Catalyst for Primary Hydroxyl Group Selective Acylation of Diols," *ACS Catalyst.*, 2017, 7:6150-6154, American Chemical Society.
Tanaka, S. et al., "Quarternary Alkyl Ammonium Salt-Catalyzed Transformation of Glycidol to Glycidyl Esters by Transesterification of Mehtyl Esters," *ACS Catalyst.*, 2018, 8:1097-1103, American Chemical Society.
Tian, S. et al., "Asymmetric Organic Catalysis with Modified Cinchona Alkaloids," *Accounts of Chemical Research*, 2004, 37(8):621-631, American Chemical Society.
Uraguchi, D. et al., "Acridinium Betaine as a Single-Electron-Transfer Catalyst: Design and Application to Dimerization of Oxindoles," *ACS Catalyst*, 2017, 7:2765-2769, American Chemical Society.
Xie, C. et al., "Natural Product Glycine Betaine as an Efficient Catalyst for Transformation of $CO_2$ with Amines to Synthesize N-Substituted Compounds," *ACS Sustainable Chemistry & Engineering*, 2017, 5:7086-7092, American Chemical Society.
Uraguchi, D. et al., "Chiral Ammonium Betaines as Ionic Nucleophilic Catalysts**," *Angew. Chem. Int. Ed.*, 2010, 49:5567-5569, Wiley-VCH Verlag GmbH & Co.
Brak, K. et al., "Asymmetric Ion-Pairing Catalysis," *Angew. Chem. Int. Ed.*, 2013, 52:534-561, Wiley-VCH Verlag GmbH & Co.
Chauhan, P. et al., "Bifunctional Amine-Squaramides: Powerful Hydrogen-Bonding Organocatalysts for Asymmetric Domino/Cascade Reactions," *Advanced Synthesis & Catalysis*, 2015, 357:253-281, Wiley-VCH GmbH & Co.
Yanai, H. et al., "Synthesis, Characterization, and Applications of Zwitterions Containing a Carbanion Moiety**," *Angew. Chem. Int. Ed.*, 2013, 52:1560-1563, Wiley-VCH Verlag GmbH & Co.
Zhang, W. et al., "A Chiral Bis(betaine) Catalyst for the Mannich Reaction of Azlactones and Aliphatic Imines**," *Angew. Chem. Int. Ed.*, 2012, 51:4085-4088, Wiley-VCH Verlag GmbH & Co.
Talebian-Kiakalaieh, A. et al., "A review on novel processes of biodiesel production from waste cooking oil," *Applied Energy*, 2013, 104:683-710, 2012 Elsevier Ltd.
Wang, H. et al., "Asymmetric cyanation of imines via dipeptide-derived organophosphine dual-reagent catalysis," *Nature Communications*, Sep. 14, 2016, 7(12720):1-9.
Liu, X. et al., "Betaine Catalysis for Hierarchical Reduction of $CO_2$ with Amines and Hydrosilane To Form Formamides, Aminals, and Methylamines," *Angew. Chem. Int. Ed.*, 2017, 56:7425-7429, Wiley-VCH Verlag GmbH & Co.
Leung, D. Y. C. et al., "A review on biodiesel production using catalyzed transesterification," *Applied Energy*, 2010, 87:1083-1095, 2009 Elsevier Ltd.

(Continued)

*Primary Examiner* — Zinna Northington Davis
(74) *Attorney, Agent, or Firm* — Saliwanchik, Lloyd & Eisenschenk

(57) ABSTRACT

An amide/iminium zwitterion catalyst has a catalyst pocket size that promotes transesterification and dehydrative esterification. The amide/iminium zwitterions are easily prepared by reacting aziridines with aminopyridines. The reaction can be applied a wide variety of esterification processes including the large-scale synthesis of biodiesel. The amide/iminium zwitterions allow the avoidance of strongly basic or acidic condition and avoidance of metal contamination in the products. Reactions are carried out at ambient or only modestly elevated temperatures. The amide/iminium zwitterion catalyst is easily recycled and reactions proceed in high to quantitative yields.

24 Claims, 12 Drawing Sheets

(56) References Cited

OTHER PUBLICATIONS

Lin, L. et al., "Opportunities and challenges for biodiesel fuel," *Applied Energy*, 2011, 88:1020-1031, 2010 Elsevier Ltd.

Kundu, D. et al., "Zwitterionic-type molten salt: An efficient mild organocatalyst for synthesis of 2-amidoalkyl and 2-carbamatoalkyl naphthols," *Catalysis Communications*, 2010, 11:1157-1159, Elsevier B.V.

Siau, W. et al., "Asymmetric organocatalytic reactions by bifunctional amine-thioureas," *Catalysis Science & Technology*, 2011, 1:1298-1310, The Royal Society of Chemistry.

Liu, X. et al., "Amide-based bifunctional organocatalysts in asymmetric reactions," *Chem. Commun.*, 2009, pp. 6145-6158, The Royal Society of Chemistry.

Yanai, H. et al., "Organic Acid Catalysts in Reactions of Lactones with Silicon Enolates," *Asian J. Org. Chem.*, 2013, 2:989-996, Wiley-VCH Verlag GmbH & Co.

Uraguchi, D. et al., "Chiral Ammonium Betaine-Catalyzed Highly Stereoselectrive Aza-Henry Reaction of α-Aryl Nitromethanes with Aromatic N-Boc Imines," *Chem. Asian J.*, 2015, 10:334-337, Wiley-VCH Verlag GmbH & Co.

Uraguchi, D. et al., "Flexible synthesis, structural determination, and synthetic application of a new $C_1$-symmetric chiral ammonium betaine†," *Chem. Commun.*, 2010, 46:300-302, The Royal Society of Chemistry.

Hatano, M. et al., "Lanthanum(III)) catalysts for highly efficient and chemoselective transesterification," *Chem. Commun.*, 2013, 49:1983-1997, The Royal Society of Chemistry.

Yanai, H. et al., "Sequential Mukaiyama-Michael reaction induced by carbon acids†," *Chem. Commun.*, 2016, 52:3280-3283, The Royal Society of Chemistry.

Guillerm, B. et al., "Ammonium betaines: efficient ionic nucleophilic catalysts for the ring-opening polymerization of $_L$-lactide and cyclic carbonates†," *Chem. Commun.*, 2014, 50:10098-10101, The Royal Society of Chemistry.

Legros, F. et al., "New Developments in Chiral Cooperative Ion Pairing Organocatalysis by Means of Ammonium Oxyanions and Fluorides: From Protonation to Deprotonation Reactions.," *Chem. Rec.*, 2017, 17:429-440, The Chemical Society of Japan & Wiley-VCH Verlag GmbH & Co. KGaA.

Qian, D. et al., "Recent Progress in Asymmetric Ion-Pairing Catalysis with Ammonium Salts," *Chem. Eur. J.*, 2019, 25:3740-3751, Wiley-VCH Verlag GmbH & Co. KGaA.

Uraguchi, D. et al., "Nitroolefins as a Nucleophilic Component for Highly Stereoselective Aza Henry Reaction under the Catalysis of Chiral Ammonium Betaines," *Chem. Eur. J.*, 2012, 18:8306-8309, Wiley-VCH Verlag GmbH & Co. KGaA.

Berg, L. et al., "The Nature of Activated Non-classical Hydrogen Bonds: A Case Study on Acetylcholinesterase-Ligand Complexes," *Chem. Eur. J.*, 2016, 22:2672-2681, Wiley-VCH Verlag GmbH & Co.

Otera, J., "Transesterification," *Chem. Rev.*, 1993, 93:1449-1470, American Chemical Society.

Molina, P. et al., "Anion Recognition Strategies Based on Combined Noncovalent Interactions," *Chem. Rev.*, 2017, 117:9907-9972, American Chemical Society.

Godemert, J. et al., "Chiral Ammonium Aryloxides: Efficient Multipurpose Basic Organocatalysts," *ChemCatChem*, 2016, 8:74-85, Wiley-VCH Verlag GmbH & Co.

Claraz, A. et al., "Asymmetric Organocatalytic Protonation of Silyl Enolates Catalyzed by Simple and Original Betaines Derived from Cinchona Alkaloids," *European Journal of Organic Chemistry*, 2013, pp. 7693-7696, Wiley-VCH Verlag GmbH & Co.

Brière, J. et al., "Recent advances in cooperative ion pairing in asymmetric organocatalysis," *Chem. Soc. Rev.*, 2012, 41:1696-1707, The Royal Society of Chemistry.

Hatano, M. et al., "Metal-Free Transesterification Catalyzed by Tetramethylammonium Methyl Carbonate," *Green Chemistry*, 2018, pp. 1-7, The Royal Society of Chemistry.

Keillor, J. W. et al., "Catalysis of Amide Hydrolysis and Formation under Neutral Conditions by a Zwitterionic Imidazolium Thiolate," *J. Am. Chem. Soc.*, 1994, 116:4669-4673, American Chemical Society.

Uraguchi, D. et al., "Chiral Ammonium Betaines: A Bifunctional Organic Base Catalyst for Asymmetric Mannich-Type Reaction of α-Nitrocarboxylates," *J. Am. Chem. Soc.*, 2008, 130:10878-10879, American Chemical Society.

Uraguchi, D. et al., "Ionic Nucleophilic Catalysis of Chiral Ammonium Betaines for Highly Stereoselective Aldol Reaction from Oxindole-Derived Vinylic Carbonates," *Journal of the American Chemical Society*, 2012, 134:6972-6975, American Chemical Society.

Zhou, X. et al., "Cinchonium Betaines as Efficient Catalysts for Asymmetric Proton Transfer Catalysis: The Development of a Practical Enantioselective Isomerization of Trifluoromethyl Imines," *Journal of the American Chemical Society*, 2016, 138:12297-12302, American Chemical Society.

Cheng, Y. A. et al., "Efficient Medium Ring Size Bromolactonization Using a Sulfur-Based Zwitterionic Organocatalyst," *Journal of the American Chemical Society*, 2012, 134:16492-16495, American Chemical Society.

Zhou, Y. et al., "Synthesis of cyclic carbonates from carbon dioxide and epoxides over betaine-based catalysts," *Journal of Molecular Catalysis A: Chemical*, 2008, 284:52-57, Elsevier B.V.

Bauer, G. et al., "Metal-Organic Frameworks Invert Molecular Reactivity: Lewis Acidic Phosphonium Zwitterions Catalyze the Aldol-Tishchenko Reaction," *Journal of the American Chemical Society*, 2017, 139:18166-18169, American Chemical Society.

Bagdi, M. R. A. K. et al., "Zwitterionic-Type Molten Salt-Catalyzed Multicomponent Reactions: One-Pot Synthesis of Substituted Imidazoles Under Solvent-Free Conditions," Sep. 2012, *Journal of Heterocyclic Chemistry*, 49:1224-1228, HeteroCorporation.

Grimme, S. et al., "Effect of the Damping Function in Dispersion Corrected Density Functional Theory," *J Comput Chem*, 2011, 32:1456-1465, Wiley Periodicals, Inc.

Hasegawa, E. et al., "Benzimidazolium Naphthoxide Betaine Is a Visible Light Promoted Organic Photoredox Catalyst," *The Journal of Organic Chemistry*, 2018, 83:3921-3927, American Chemical Society.

Ishihara, K. et al., "Zwitterionic Salts as Mild Organocatalysts for Transesterification," *Organic Letters*, 2008, 11(11):2187-2190, American Chemical Society.

Phipps, R. J. et al., "The progression of chiral anions from concepts to applications in asymmetric catalysis," *Nature Chemistry*, Aug. 2012, 4:603-614, Macmillan Publishers Limited.

Uraguchi, D. et al., "Performance of $C_1$-symmetric chiral ammonium betaines as catalysts for the enantioselective Mannich-type reaction of α-nitrocarboxylates," *Tetrahedron: Asymmetry*, 2010, 21:1189-1190, Elsevier Ltd.

Chen, K. et al., "Design of Betaine Functional Catalyst for Efficient Copolymerization of Oxirane and $CO_2$," *Macromolecules*, 2018, 51:6057-6062, American Chemical Society.

Tsutsumi, Y. et al., "Bifunctional Organocatalyst for Activation of Carbon Dioxide and Epoxide To Produce Cyclic Carbonate: Betaine as a New Catalytic Motif," *Organic Letters*, 2010, 12(24):5728-5731, American Chemical Society.

Johnston, R. C. et al., "C-H•••O non-classical hydrogen bonding in the stereomechanics of organic transformations: theory and recognition†," *Organic & Biomolecular Chemistry*, 2013, 11:5057-5064, The Royal Society of Chemistry.

Kundu, D., et al., "Zwitterionic-Type Molten Salt: A Mild and Efficient Organocatalyst for the Synthesis of 3-Aminoalkylated Indoles via Three-Component Coupling Reaction," *Synlett*, 2011, 8:1164-1167, Georg Thieme Verlag Stuttgart.

Rahman, M. et al., "Organocatalysis by an aprotic imidazolium zwitterion: a dramatic anion-cation cooperative effect on azide-nitrile cycloaddition†," *RSC Advances*, 2014, 4:6116-6119, The Royal Society of Chemistry.

Qiao, Y. et al., "Chiral Zwitterions from Vicinal Diamines: Effective and Recoverable Asymmetric Enamine Catalysts," *Synlett*, 2011, 4:495-498, Georg Thieme Verlag Stuttgart.

(56) References Cited

OTHER PUBLICATIONS

Gupta, M. et al., "Scope and opportunities of using glycerol as an energy source," *Renewable and Sustainable Energy Reviews*, 2012, 16:4551-4556, Elsevier Ltd.

Feng, H. et al., "Block Copolymers: Synthesis, Self-Assembly, and Applications," *Polymers*, 2017, 9(494):1-31.

Xiong, X. et al., "Zwitterionic-Salt-Catalyzed Site-Selective Monobromination of Arenes," *Organic Letters*, 2017, 19:4243-4246, American Chemical Society.

"Working with Hazardous Chemicals," *Organic Syntheses*, 2010, 87:161-169, Organic Syntheses, Inc.

Yanai, H. et al., "Chemoselective Two-Directional Reaction of Bifunctionalized Sub-strates: Formal Ketal-Selective Mukaiyama Aldol Type Reaction," *Synlett*, 2015, 26:2457-2461, Georg Thieme Verlaq Stuttgart.

Kundu, D. et al., "Zwitterionic-type molten salt-catalyzed syn-selective aza-Henry reaction: solvent-free one-pot synthesis of β-nitroamines," *Tetrahedron Letters*, 2009, 50:6998-7000, Elsevier Ltd.

Zhao, Y. et al., "The M06 suite of density functionals for main group thermochemistry, thermochemical kinetics, noncovalent interactions, excited states, and transition elements: two new functionals and systematic testing of four M06-class functionals and 12 other functionals," *Theor Chem Account*, 2008, 120:215-241, Springer-Verlag 2007.

Office Action dated Nov. 10, 2022 in Chinese Application No. 202010704459.5.

\* cited by examiner

5a

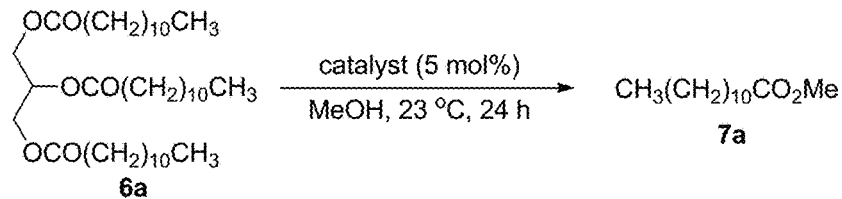

| catalyst | yield of 7a | catalyst | yield of 7a | catalyst | yield of 7a |
|---|---|---|---|---|---|
| 3b | 0% | 5f | 0% | Et$_3$N | trace[c] |
| 5a | 70% | 5g | 0% | DMAP | trace[c] |
| 5b | 72% | 5h | 0% | PPY | trace[c] |
| 5c | 79% | 5i | 0% | PPh$_3$ | trace |
| 5d | >99% | 5j | 60% | TBAI | trace |
| 5d | 99%[a] | 5k | 74% | [(n-dodec)$_3$MeN]$^+$Cl$^-$ | 0% |
| 5d | 99%[b] 50 g scale | NaOMe | 32%[c] | [Me$_4$N]$^+$[OCO$_2$Me]$^-$ | trace |
| 5e | 0% | tBuOK | 52%[c] | | |

[a]Reaction was done using 2 mol% of 5d at 70 °C for 2 h. [b]Reaction was done using 2.5 mol% of 5d for 96 h. [c]Reaction was done at 70 °C.

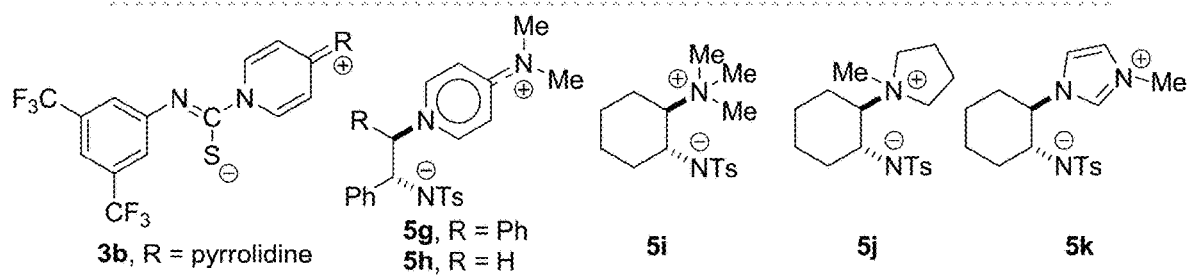

FIG. 4

| | | substrate | R | product | yield |
|---|---|---|---|---|---|
| | | 6b | CH$_3$ | 7b | 99% |
| | | 6c | CH$_3$(CH$_2$)$_3$ | 7c | 99% |
| | | 6d | CH$_3$(CH$_2$)$_6$ | 7d | 99% |
| | | 6e | CH$_3$(CH$_2$)$_{12}$ | 7e | 99% |
| | | 6f | CH$_3$(CH$_2$)$_7$⁀(CH$_2$)$_7$ | 7f | 99% |

ZWITTERIONIC CATALYSTS FOR (TRANS)ESTERIFICATION: APPLICATION IN FLUOROINDOLE-DERIVATIVES AND BIODIESEL SYNTHESIS

CROSS-REFERENCE TO RELATED APPLICATION

This application claims the benefit of U.S. Provisional Application Ser. No. 62/878,044, filed Jul. 24, 2019, the disclosure of which is hereby incorporated by reference in its entirety, including all figures, tables and drawings.

BACKGROUND OF THE INVENTION

Bifunctional organocatalysts play an increasingly important role in organic synthesis. A cooperative effect between the functional groups in the bifunctional systems brings the pair of reactants into close proximity for efficient chemical transformations. Constitutional components, such as Brønsted bases/acids, Lewis bases, dihydrogen bonds, and cooperative ion pairing, are frequently included in the design of bifunctional organocatalysts. An emerging class of bifunctional organocatalysts is zwitterions, which are referred to as inner salts, where an anion and a cation are site-isolated within a single molecule and the ion pair works synergistically to activate the reaction partners. Catalysis using zwitterions remain underexploited, partly because of the difficulty of identifying suitable catalyst architectures and the difficulty in preparing zwitterionic catalysts.

Among the reported zwitterion catalytic systems, oxide-containing zwitterions are the most studied. For example, betaines, with oxide and ammonium, derived from a number of skeletons have been used for a range of catalytic processes, such as, $CO_2$ fixation, polymerization, photoredox reactions, Aldol/Mannich-type reactions, and aziridine opening. Recently, asymmetric catalytic reactions using chiral quaternary ammonium betaines have been reported in Uraguchi et al., *Angew. Chem. Int. Ed.* 2010, 49, 5567-9, Zhou et al., *J. Am. Chem. Soc.* 2016, 138, 12297-302, Zhang et al., *Angew. Chem. Int. Ed.* 2012, 51, 4085-8, and Claraz et al., *Eur. J. Org. Chem.* 2013, 7693-6. A betaine Co(III) complex has been reported for copolymerization in Chen et al., *Macromolecules* 2018, 51, 6057-6062. In situ generated oxide/phosphonium zwitterionic catalysts are applicable for: Mannich-type reactions; Strecker-type reactions; Aldol-Tishchenko reactions, with the influence of metal-organic frameworks; and primary hydroxyl group selective acylation of diols, with aromatic oxides.

Zwitterionic catalysts containing ion pairs other than ammonium betaines are very rare, but include imidazolium thiolate catalysts for amide hydrolysis, zwitterionic carbon acids for some acid-catalyzed transformations and a sulfide/iminium zwitterion that promotes transesterification, including medium-ring lactonization of olefinic acids, and electrophilic halogention of arenes. The sulfide/iminium zwitterion:

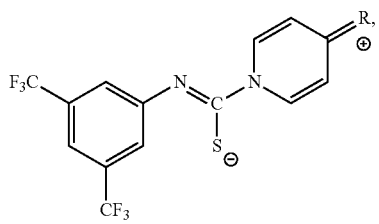

where R is $N(CH_3)_2$ or pyrrolidone is an attractive catalyst platform easily prepared through nucleophilic addition of an isothiocyanate by a 4-aminopyridine to form a structurally well-defined charge pair system, as reported by Ishihara et al. *Org. Lett.* 2008, 10, 2187-90. The sulfide/iminium zwitterion allows effective interaction as a catalyst with complementary reagents. Unfortunately, this sulfide zwitterion exists in equilibrium with its precursors in solution, which allows the isothiocyanate to be hydrated in the presence of moisture, which limited its efficacy in many situations. To overcome this stability limitation other iminium zwitterions are required. To this end, a new class of zwitterionic organocatalysts, structurally stable amide anion/iminium cation based zwitterions are presented.

BRIEF SUMMARY OF THE INVENTION

An embodiment of the invention is directed to stable amide/iminium zwitterionic catalyst. In an embodiment of the invention the amide/iminium zwitterionic catalyst is synthesized by adding aziridines with aminopyridines. In another embodiment of the invention, transesterification or esterification is carried out in the presence of the amide/iminium zwitterionic catalyst to form a desired ester. In an embodiment of the invention, the ester is a fluoroindole-derivative formed by transesterification. In one embodiment of the invention the ester is a biodiesel that is synthesized without metal contamination, which is formed by dissolving triglycerides and the zwitterionic catalyst in a solvent at room temperature followed by combining the solvent with water and an ester. Subsequently, upon extraction and removal of volatiles, a usable biodiesel product is obtained directly. In one embodiment the ester is a dialkyl succinic formed by the reaction of the alkyl alcohol with succinic anhydride, or an equivalent, by the ring-opening of other cyclic acid anhydrides.

BRIEF DESCRIPTION OF THE DRAWINGS

FIG. 4 shows a reaction scheme for the transesterification of a triglyceride with methanol to a fatty acid methyl ester (FAME), according to an embodiment of the invention and a table for the comparative yields employing the amide/iminium zwitterionic catalysts according to embodiments of the invention and other prior art catalysts under equivalent conditions.

FIG. 5 shows a reaction scheme for the transesterification of triglycerides with methanol to FAMEs, according to an embodiment of the invention, and a table for the comparative yields employing the amide/iminium zwitterionic catalyst 5d, according to embodiments of the invention, for various units on the esters.

FIG. 10 shows a reaction scheme for the transesterification of various carboxylic acid esters with various alcohols, according to an embodiment of the invention, and a table for the yields employing the amide/iminium zwitterionic catalyst 5d, according to embodiments of the invention.

DETAILED DISCLOSURE OF THE INVENTION

A new class of a zwitterionic catalyst comprises an amide/iminium zwitterion that separates the center of the charges on a sulfonamide and the iminium derived from a 4-aminopyridine by three to seven bonds, according to an embodiment of the invention. An amide/iminium zwitterionic catalyst, according to an embodiment of the invention has the structure:

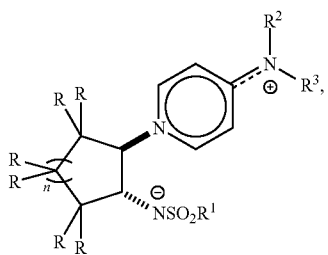

where: n is 1, 2, 3, or 4; R is independently H, aryl, $C_1$ to $C_6$ alkyl substituted aryl, $C_1$ to $C_6$ alkyl, aryl substituted $C_1$ to $C_6$ alkyl, wherein any of the carbons of the alky or aryl groups is unsubstituted or substituted with a $C_1$ to $C_6$ alkyl ether, aryl ether, $C_1$ to $C_6$ alkyl thioether, aryl thioether and where the alkyl is straight, branched, or cyclo alkyl, and where any of the alkyl groups may be interrupted one or more times with an O or S; $R^1$ is aryl, nitro substituted aryl, $C_1$ to $C_6$ alkyl substituted aryl, $C_1$ to $C_6$ alkyl, or $C_1$ to $C_6$ perfluoroalkyl; and $R^2$ and $R^3$ are independently $C_1$ to $C_6$ alkyl or in combination form a 5- or 6-membered ring heterocyclic ring with the iminium nitrogen, where the ring is optionally interrupted with one or more O or NR' units, where R' is aryl, $C_1$ to $C_6$ alkyl substituted aryl, or $C_1$ to $C_6$ alkyl. In an exemplary embodiment of the invention, $SO_2R^1$ is tosyl or mesyl and $R^2$ and $R^3$ are methyl or $NR^2R^3$ are combined as pyrrolidone (PPY), as indicated below:

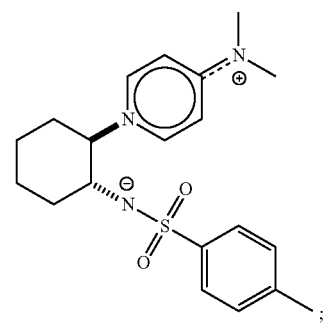

5a

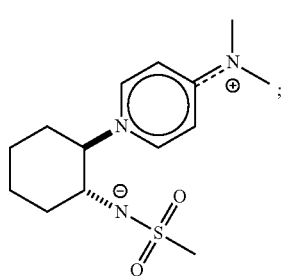

5b

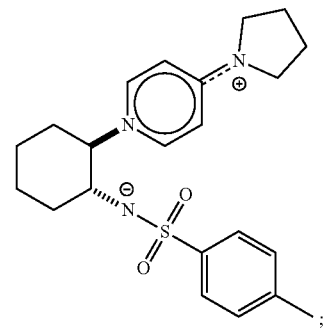

5c

-continued

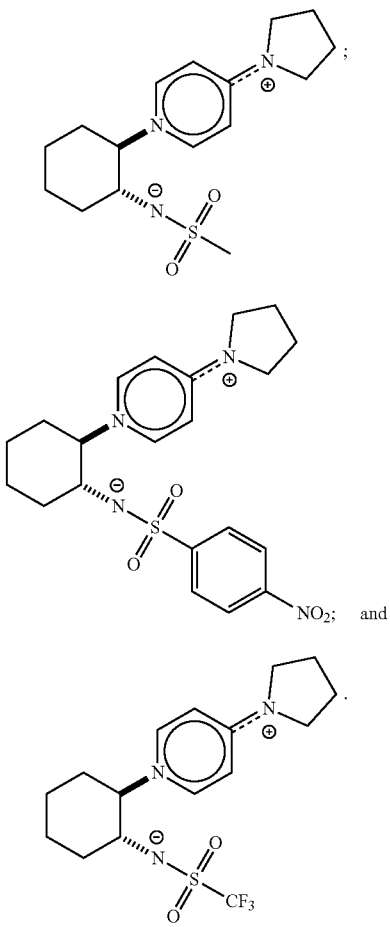

Figure 1:
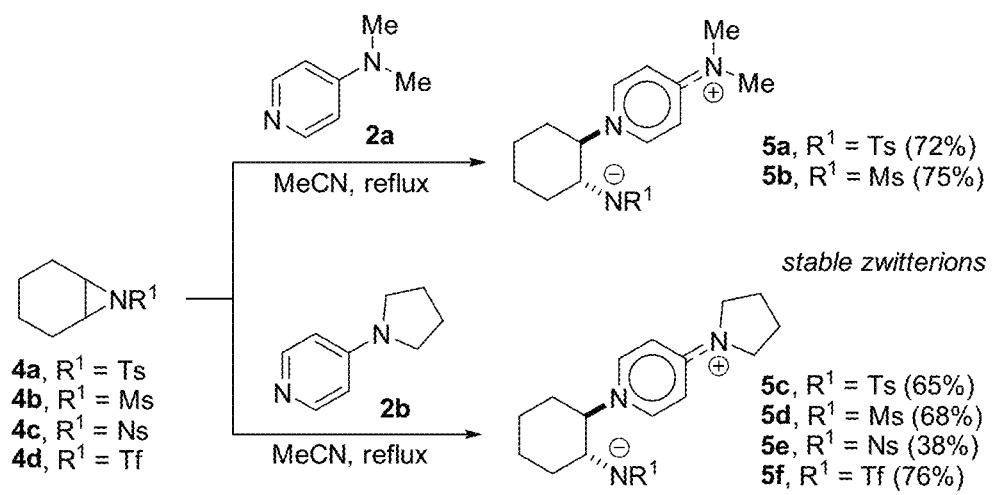
FIG. 1 shows a reaction scheme for an exemplary preparation of amide/iminium zwitterionic catalysts, according to embodiments of the invention.
Figure 2:
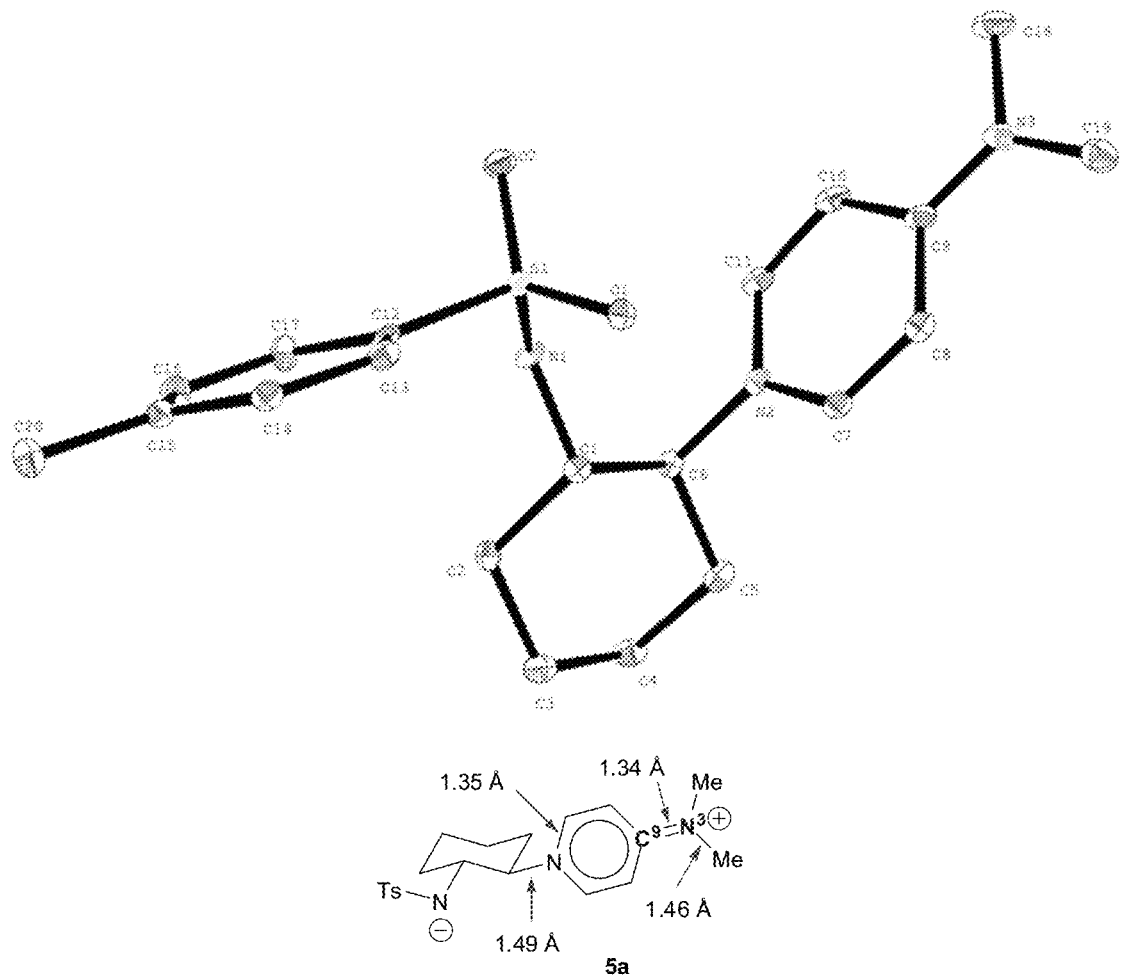
FIG. 2 shows an X-ray crystallographic structure on a single crystal of zwitterion 5a, according to an embodiment of the invention.
Figure 3:
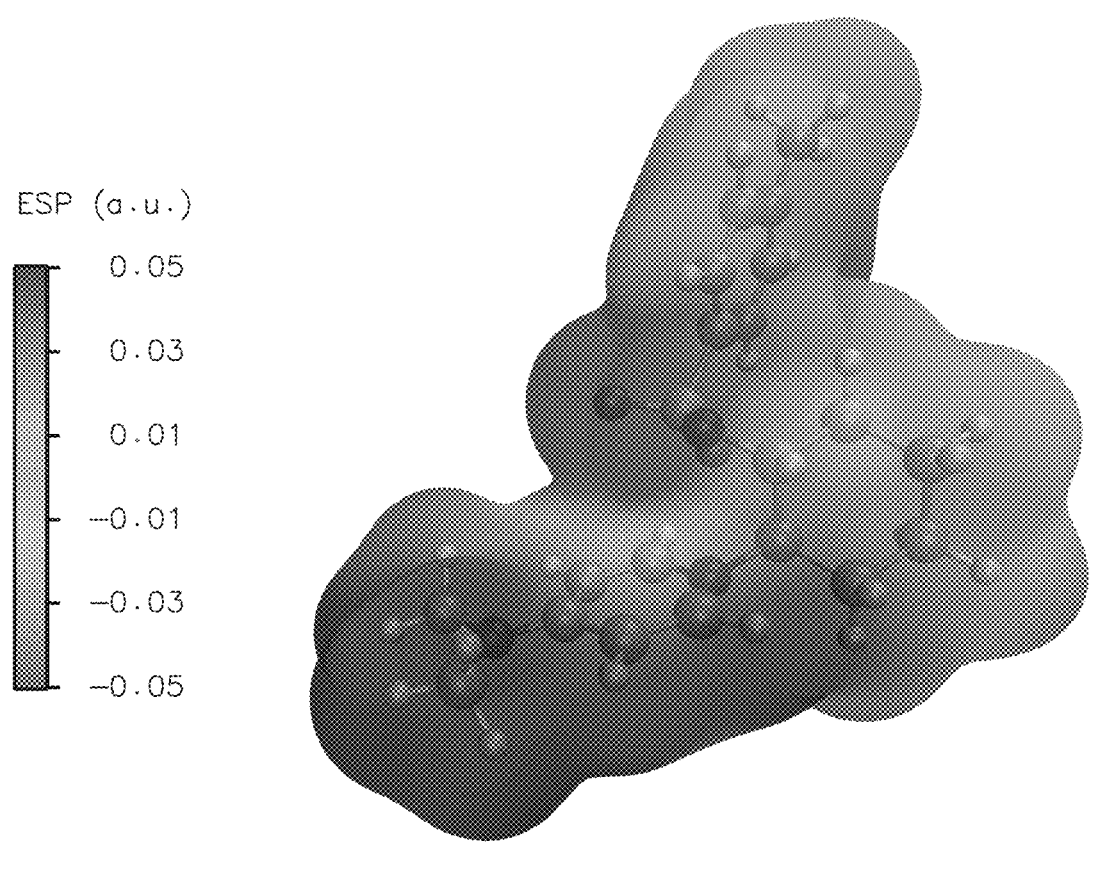
FIG. 3 shows an in silico structure of 5a indicating the electrostatic potential within the amide/iminium zwitterionic catalyst, according to an embodiment of the invention.

In an embodiment of the invention, preparation of the amide/iminium zwitterionic catalyst occurs by nucleophilic attack of a bicyclic aziridine by a 4-aminopyridine, as shown in FIG. 1. The release the ring-strain and result in the energetically more favorable zwitterion, which inhibits the reverse reaction. The N-sulfonated aziridines is readily prepared from the cycloalkyl imine which is readily formed as disclosed in Watson et al., Org. Synth. 2010, 87, 161-9. The tosyl aziridine 4a is opened by 4-(N,N-dimethylamino) pyridine (DMAP, 2a) in refluxing acetonitrile to give zwitterion 5a in 72% yield, as shown in FIG. 1. In like manner, by changing the N-sulfonamide at aziridine and/or the aminopyridine analogues 5b-5f are formed. An X-ray crystallographic structure on a single crystal of zwitterion 5a is shown in FIG. 2. The N(3)-C(9) iminium bond length of 1.34 Å, from the X-ray data is significantly shorter than a typical C—N single bond, consistent with the bonding having considerable C=N character with the N(3) nitrogen being positively charged. The electropositivity of the iminium cation appears to be considerably enhanced because the counteranion sulfonamide is effectively dissociated to a large extent because of its site isolation in the carbon skeleton. Computations on the electrostatic potential of 5a also indicated that the iminium moiety possesses considerable positive charge, as illustrated in FIG. 3. Zwitterions 5a-5f are structurally stable with no decomposition was observed upon heating, consistent with the pyridinium moiety and sulfonamide residing in equational positions inhibiting decomposition by substitution or Hoffmann elimination. Advantageously, zwitterions 5a-5f are not hygroscopic and are easily handled to perform catalytic reactions.

In an embodiment of the invention, the amide/iminium zwitterionic catalyst promotes transesterification of triglycerides to fatty acid methyl esters (FAMEs), which are commonly used as biodiesel. As shown in FIG. 4, FAMEs are formed when a fatty acid ester 6a is suspended in MeOH with 5 mol % of various amide/iminium zwitterionic catalysts at 23° C. The transesterification proceeds smoothly and FAME 7a is obtained in 70-79% isolated yield when using zwitterions 5a-c. The efficiency is very high when using zwitterion 5d bearing both a mesyl and a PPY. The reaction can be run with a low catalyst loading, for example, 2 mol % of 5d, at 70° C. for 2 h, giving FAME 7a in 99% yield. When performed at larger scales, the reaction yielded 7a quantitatively. In sharp contrast, no reaction was observed when using a prior art sulfide/iminium zwitterion, 3b, as the catalyst, presumably due to decomposition of the catalyst through methanolysis of the isothiocyanate in equilibrium with the zwitterion. Alternative zwitterions 5e-f bearing more electron-deficient sulfonamides, 5g-h displaying different skeleton rigidity and 5i-k displaying different distance between the cation and anion, were prepared using a similar method to that in 5a-d, display inferior performance to 5d. These results suggest that the structurally rigidity imposed by the cycloalkyl ring with equatorial positions for the sulfonamide and pyridyl substituents and the cation/anion distance that is found in 5d is an important factor for catalytic performance. Likewise, other catalysts including Brønsted bases (NaOMe, tBuOK), Lewis bases (Et$_3$N, DMAP, PPY, PPh$_3$), and ammonium salts (tetra-n-butylammonium iodide (TBAI), tri-n-dodecylmethylammonium chloride, and tetramethylammonium methyl carbonate) are much less effective for promoting the transesterification reaction under equivalent conditions.

The transesterification of triglycerides is applicable to other fatty acid esters, for example, as shown in FIG. 5, 6b-f. For the case of 6f, the corresponding FAME 7f is obtained in quantitative yield with the unsaturated system remaining intact. The glycosides used for the formation of FAMEs, according to an embodiment of the invention, can have the structure:

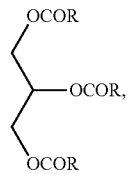

where R is independently a straight or branched C$_1$ to C$_{26}$ alkyl chain, straight or branched C$_3$ to C$_{26}$ alkenyl chain having 1 to 6 degrees of unsaturation. Among a non-exclusive list of fatty acids that can be a portion of the triglyceride include, but are not limited to butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid; arachidic acid, heneicosylic acid, behenic acid, tricosylic acid, lignoceric acid, pentacosylic acid, cerotic acid, carboceric acid, montanic acid, nonacosylic acid, melissic acid, hentriacontylic acid, lacceroic acid, psyllic acid, geddic acid, ceroplastic acid, hexatriacontylic acid, heptatriacontylic acid, octatriacontylic acid, nonatriacontylic acid, tetracontylic acid, α-linolenic acid, stearidonic acid, eicosapentaenoic acid, docosahexaenoic acid, linoleic acid, linolelaidic acid, γ-linolenic acid, dihomo-γ-linolenic acid, arachidonic acid, docosatetraenoic acid, palmitoleic acid, vaccenic acid, paullinic acid, oleic acid, elaidic acid, gondoic acid, erucic acid, nervonic acid, and mead acid. The alcohol used for the formation of the FAMEs, according to an embodiment of the invention, can include any $C_1$ to $C_{10}$ alcohol, including, but not limited to, methanol, ethanol, 1-propanol, n-butanol, isobutanol, 1-pentanol, isoamyl alcohol, 2-methyl-1-butanol, 1-hexanol, 1-heptanol, 1-octanol, 1-nonanol, 1-decanol, benzyl alcohol, or phenethyl alcohol.

Figure 6:
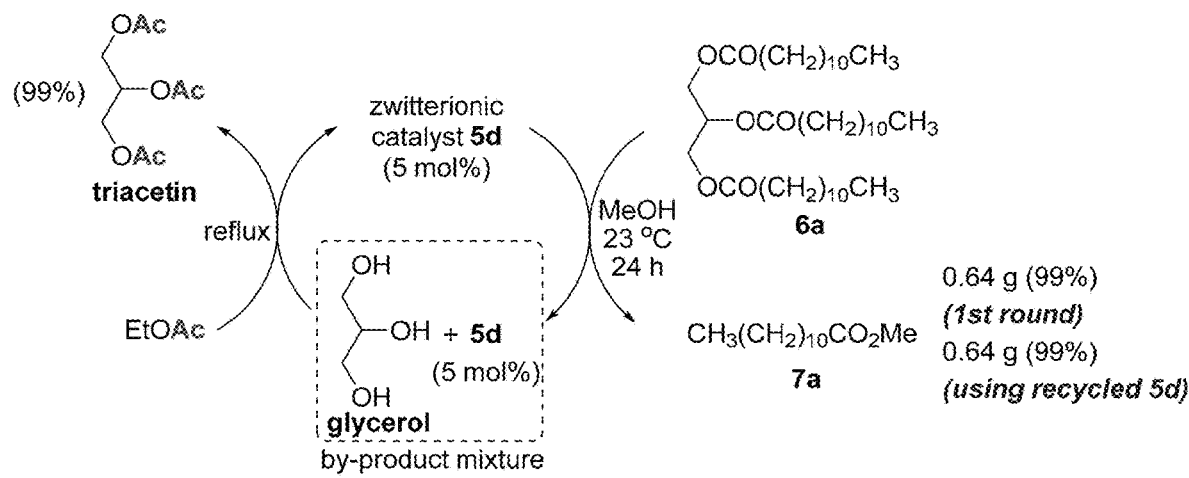
FIG. 6 shows a recycling reaction scheme for the transesterification of a triglyceride with methanol to a FAME with the conversion of the by-product glycerol to triacetin, according to an embodiment of the invention.

FAME 6a is easily separated by aqueous washing to remove the glycerol and zwitterionic catalyst 5d. The by-product mixture containing glycerol, commonly a large by-product in the production of biodiesel, in the presence of catalyst 5d undergoes transesterification with ethyl acetate to give triacetin in high yield, as indicated in FIG. 6, which can be used as a biodiesel additive, an antiknock agent, or isolated for use as a food additive or plasticizer. The zwitterionic catalyst 5d is readily recycled and reused in a subsequent FAME 7 synthesis with similar catalyst performance, as shown in FIG. 6. In contrast to other FAME preparation methods, such as base-catalyzed transesterification that requires anhydrous conditions to avoid hydrolysis of the ester to form carboxylic acid, and catalyst-free transesterification in supercritical MeOH that requires high temperature/pressure and special equipment, this virtually neutral amide/iminium zwitterionic catalyst promoted production can be operated without the need of excluding moisture or using anhydrous alcoholic solvents. As clean conversion is achieved using conventional apparatus at ambient conditions of 1 atm and 23° C., the synthesis of biodiesel is readily scalable under mild conditions.

Figure 7:
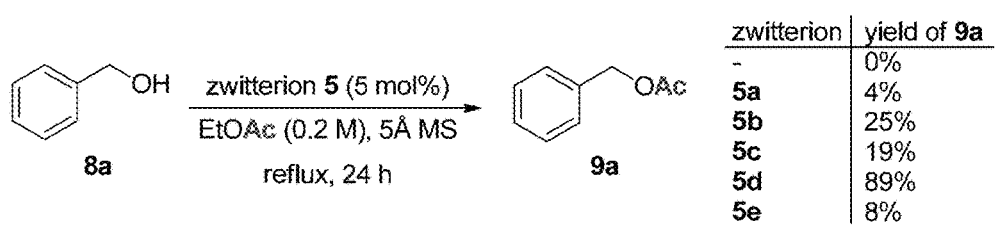
FIG. 7 shows a reaction scheme for the transesterification of benzyl alcohol with ethyl acetate to form benzyl acetate using various amide/iminium zwitterionic catalysts, according to embodiments of the invention.
Figure 8:
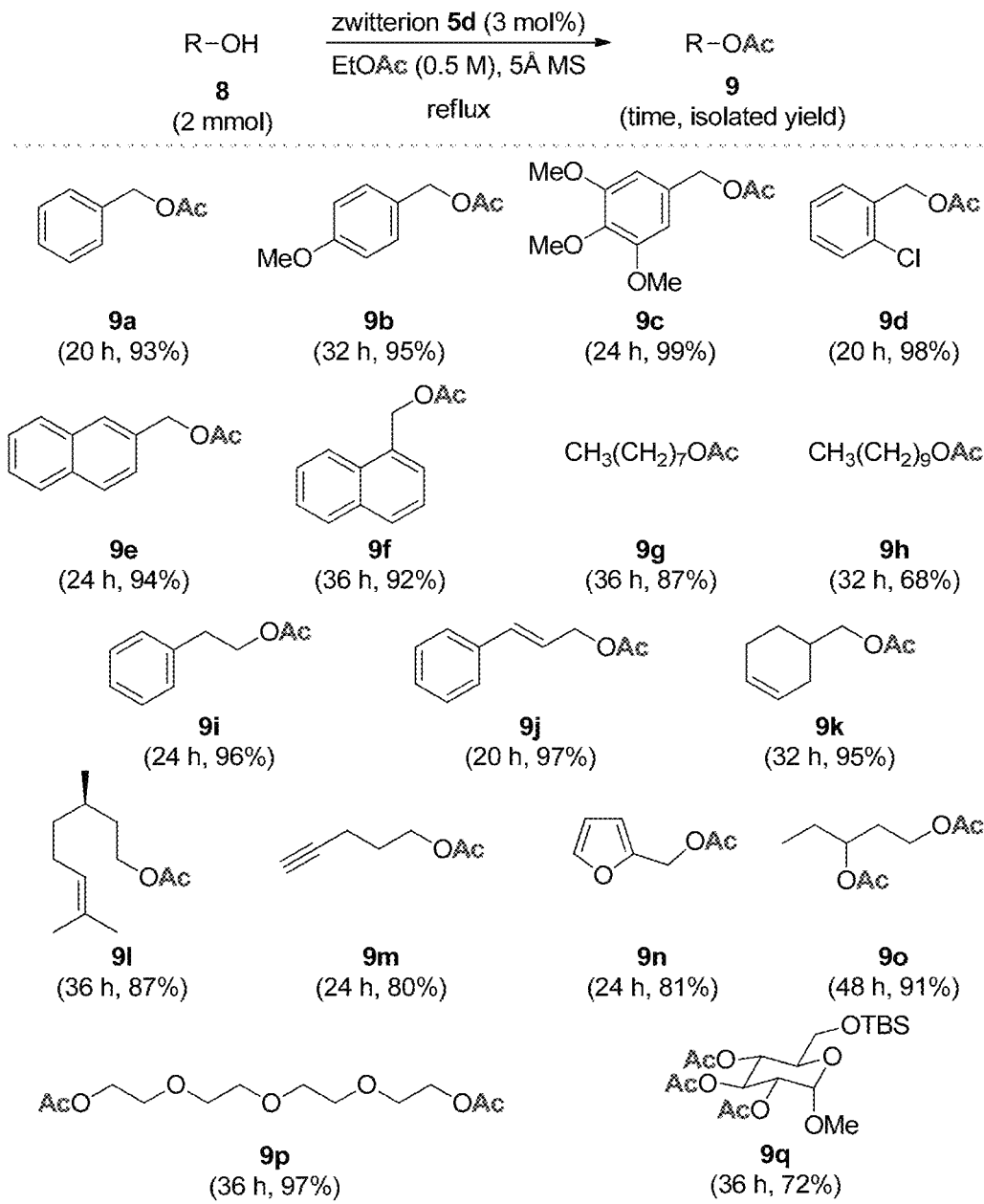
FIG. 8 shows a reaction scheme for the transesterification of ethyl acetate with various alcohols to form acetate esters of the alcohols using the amide/iminium zwitterionic catalyst 5d, according to an embodiment of the invention.
Figure 9:
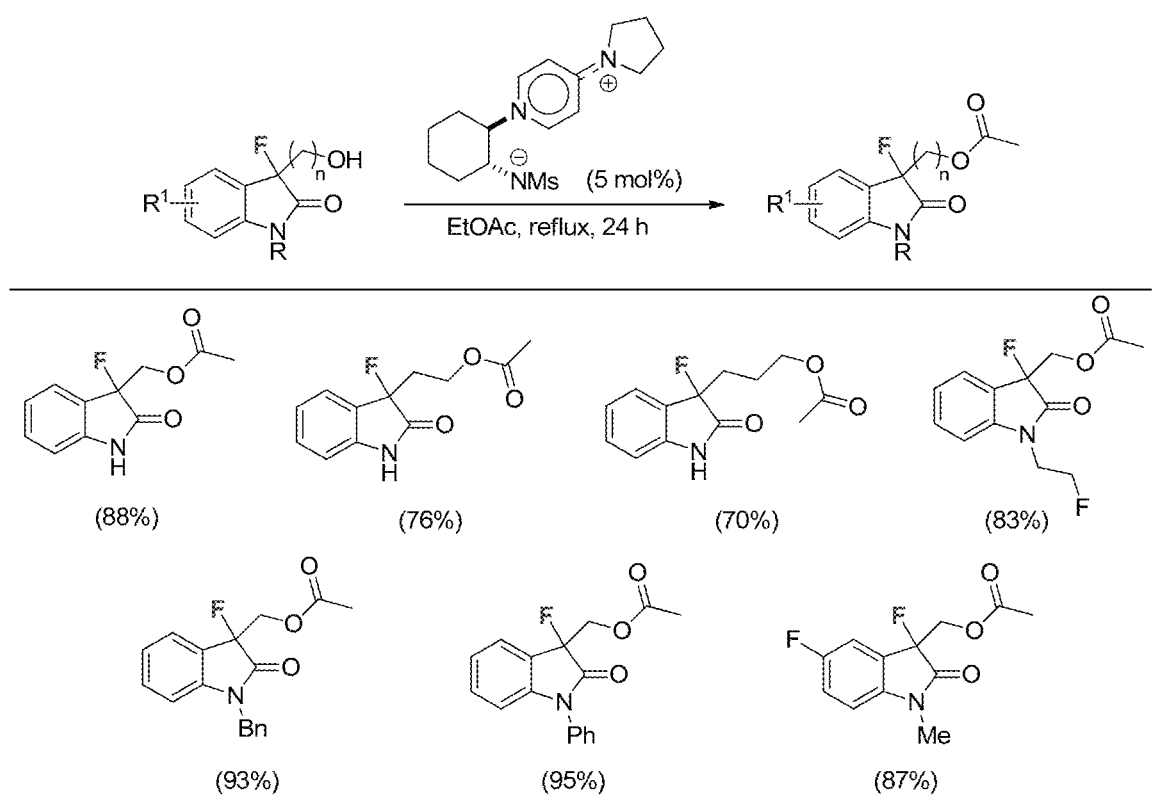
FIG. 9 shows a reaction scheme for the transesterification of ethyl acetate with various fluoroindoles using the amide/iminium zwitterionic catalyst 5d and the yields of the various resulting esters, according to an embodiment of the invention.
Figure 10:
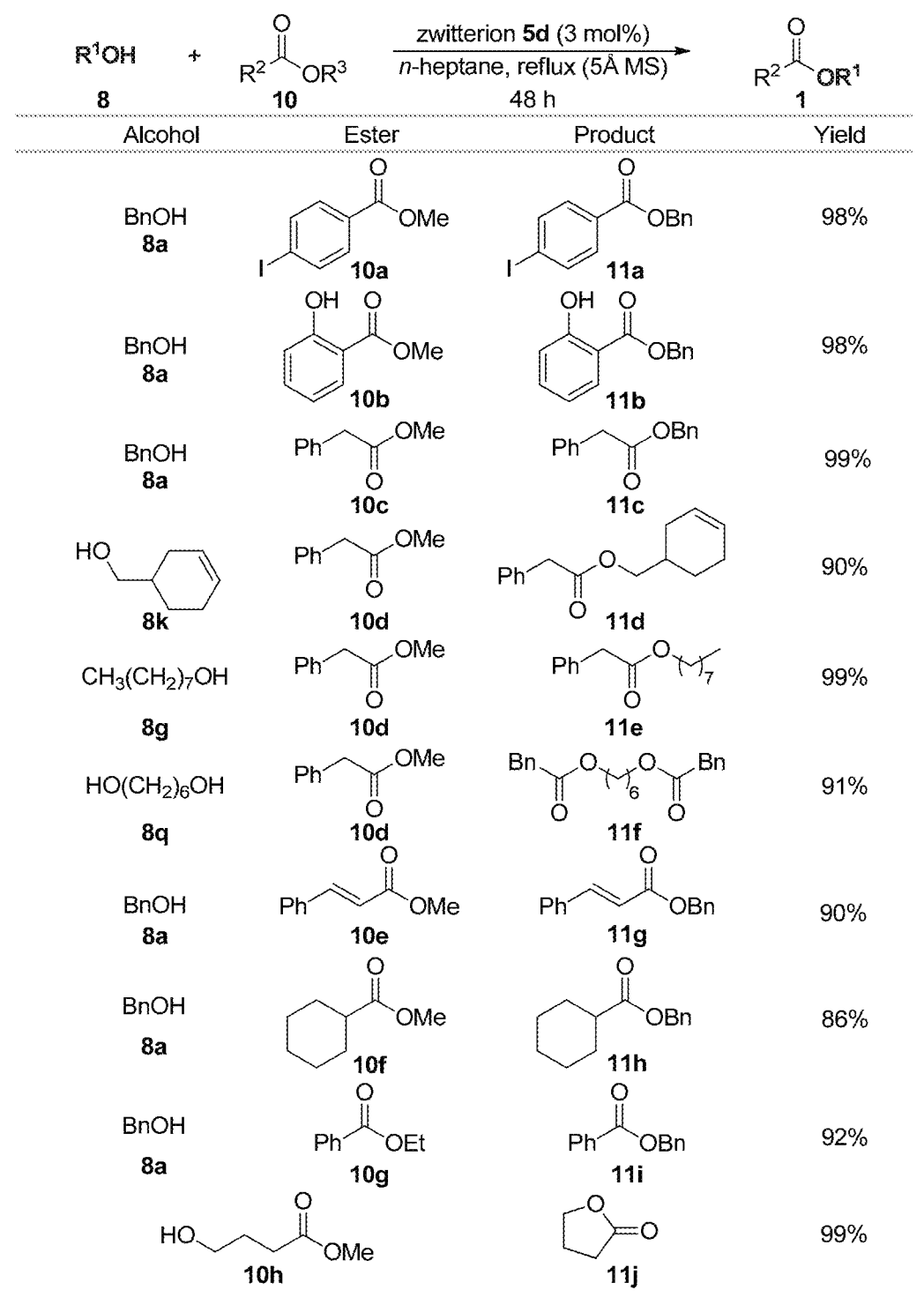

Amide/iminium zwitterionic catalysts, such as 5d, catalyze transesterification of monoesters with alcohols, according to an embodiment of the invention. As shown in FIG. 7, benzyl alcohol 8a undergoes reaction in refluxing ethyl acetate employing 5 Å molecular sieves to remove the ethanol formed as a by-product. As in the case of the FAMEs synthesis, catalytic performance of 5d is superior to other analogues. The transesterification reaction proceeds smoothly using 3 mol % of zwitterion 5d at a higher reagent concentration with benzyl alcohol and other alcohols, as shown in FIG. 8. The reaction proceeds smoothly with various aliphatic alcohols 8a-i having electron-donating or electron-withdrawing substituents. Where the alcohol contains functionalities that are sensitive to conventional acid-mediated transesterification conditions, including alkene 8j-l, alkyne 8m, and furan 8n are used, compatibility with the zwitterion-catalyzed system allows the formation of the corresponding acetate products 9j-n in good-to-excellent isolated yields. Acetylation of diols 8o and 8p yields diacetates 9o (91%) and 9p (97%). The triacetylated sugar derivative 9q forms in good isolated yield. In contrast to common acetylation of alcohols, the most common protection methods during complex synthesis, which requires the use of acetyl chloride or acetic anhydride, the transesterification according to embodiments of the invention, easily introduce the protecting group acetate into alcohols without imposing acidic conditions. The amide/iminium zwitterionic catalyzed transesterification can be extended to fluoroindole-derivatives, according to an embodiment of the invention, as shown in FIG. 9. Transesterification of methyl esters with different alcohol partners, according to an embodiment of the invention, allows the reaction of equal molar amounts of alcohols 8 and methyl esters 10 while removing the methanol as an azeotrope, for example with refluxing n-heptane, as shown in the table in FIG. 10. The transesterification is compatible with various functionalities. For example, methyl salicylate (10b) readily undergoes transesterification with benzyl alcohol (8a) to give 11b in 98% yield. A 2:1 mixture of methyl ester 10d and diol 8q gives the transesterified diester product 11f in 91% yield. The catalytic protocol is compatible with α,β-unsaturated esters, 10e, bulky esters, 10f, and ethyl esters, 10g. After three hours, at the concentrations employed (0.25 M), lactone 11j was obtained quantitatively through the intramolecular transesterification of hydroxyl ester 10h.

Among the alcohols that can be used for the transesterification with carboxylic acid esters, according to an embodiment of the invention, include, but are not limited to primary or secondary $C_1$ to $C_{30}$ alcohols of the structure $HOC(H)_x R_{3-x}$ where x is 1 to 3 and R is independently liner, branched, or cyclic alkyl; liner, branched, or cyclic alkenyl; liner, branched, or cyclic alkynyl; aryl; liner, branched, or cyclic alkylaryl; liner, branched, or cyclic alkenylaryl; liner, branched, or cyclic alkynylaryl; N, O and/or S comprising heterocycle having one to four hetero atoms, where the carbons of R can be interrupted with one or more times with O, S, C(O), NR", or C(O)NR", and where any of the carbon atoms of R can be substituted with a, $C_1$ to $C_{10}$ liner, branched, or cyclic alkyl, liner, branched, or cyclic alkenyl, liner, branched, or cyclic alkynyl, aryl, liner, branched, or cyclic alkylaryl, liner, branched, or cyclic alkenylaryl, liner, branched, or cyclic alkynylaryl, N, O and/or S comprising heterocycle having one or more hetero atoms, halogen, alkoxy, R"$_2$N where R" is independently aryl, $C_1$ to $C_{10}$ alkyl, or $C_1$ to $C_{10}$ alkenyl. Alcohols include primary and secondary ols, diols, triols, and polyols, where mono-, di-, tri-, or poly-esters are formed. The polyol can be a carbohydrate, including monosaccharides, disaccharides, and polyols such as, but not limited to, glucose, galactose, fructose, xylose, sucrose, lactose, maltose, trehalose, sorbitol, and mannitol. The esters can have the structure: RC(O)OR' where: R is selected from, but not limited to, H, liner, branched, or cyclic alkyl; liner, branched, or cyclic alkenyl; liner, branched, or cyclic alkynyl; aryl; liner, branched, or cyclic alkylaryl; liner, branched, or cyclic alkenylaryl; liner, branched, or cyclic alkynylaryl; N, O and/or S comprising heterocycle having one to four hetero atoms, where the carbons of R can be interrupted with one or more times with O, S, C(O), or C(O)NR" where R" is independently aryl, $C_1$ to $C_{10}$ alkyl, or $C_1$ to $C_{10}$ alkenyl, and where any of the carbon atoms of R can be substituted with a, $C_1$ to $C_{10}$ liner, branched, or cyclic alkyl, liner, branched, or cyclic alkenyl, liner, branched, or cyclic alkynyl, aryl, liner, branched, or cyclic alkylaryl, liner, branched, or cyclic alkenylaryl, liner, branched, or cyclic alkynylaryl, N, O and/or S comprising heterocycle having one to four hetero atoms, halogen, and alkoxy; and R' is selected from methyl, ethyl, n-propyl, i-propyl, n-butyl, i-butyl, sec-butyl, tert-butyl or neo-pentyl.

Figure 11:
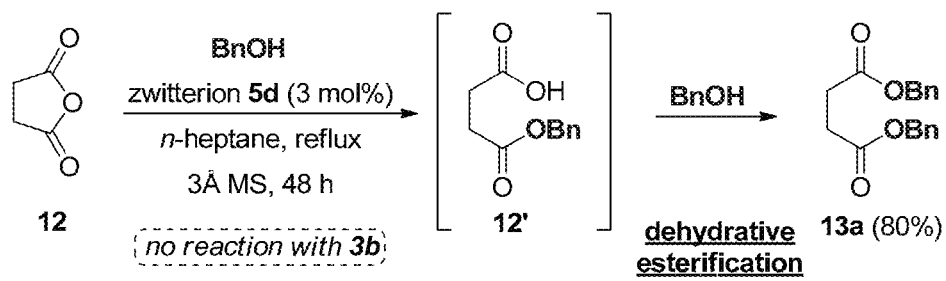
FIG. 11 shows a reaction scheme for the esterification of succinic anhydride with benzyl alcohol, according to an embodiment of the invention.
Figure 12:
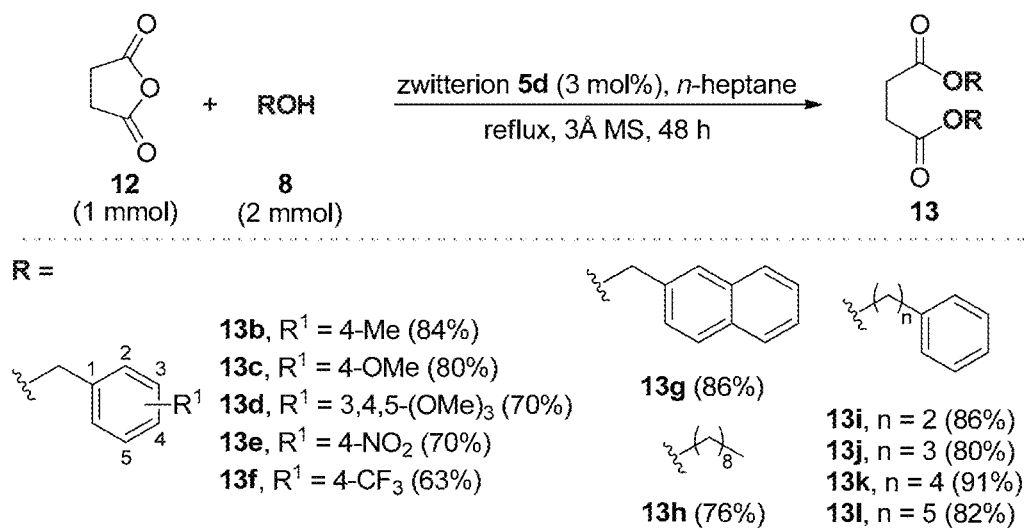
FIG. 12 shows reaction schemes for the esterification of succinic anhydrides with various alcohols employing the amide/iminium zwitterionic catalyst 5d, according to an embodiment of the invention.
Figure 13:
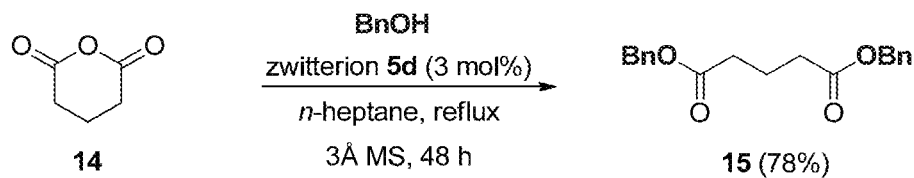
FIG. 13 shows reaction schemes for the esterification of glutaric anhydride with benzyl alcohol, according to an embodiment of the invention.

Amide/iminium zwitterionic catalyst, according to an embodiment of the invention, promotes reaction between anhydrides, for example, succinic anhydride 12, and alcohols, for example, benzyl alcohol, BnOH, 8a, to give diesters, for example 13a, as shown in FIG. 11. The reaction occurs through a one-pot two-step sequence of (1) ring-opening of 12 by 8a to yield mono-ester 12' followed by (2) dehydrative esterification of 12' to give diester 13a. The generality of this reaction system, according to an embodiment of the invention, is indicated in FIG. 12. The reactions can performed in refluxing n-heptane with a Dean-Stark apparatus to remove the water by-product in the dehydrative esterification step. A wide range of alcohols 8 bearing electron-rich or electron-deficient substituents are compatible and the corresponding diester products 13b-13l are obtained in good isolated yields under mild conditions. When replacing succinic anhydride (12) with glutaric anhydride (14), the corresponding diester 15 is obtained in a similar, 78% yield, as indicated in FIG. 13. Diesters, useful starting materials for block co-polymer production, generally are synthesized using harsh conditions. Among the anhydrides that can be used for esterification catalyzed by the amide/iminium zwitterionic catalysts include, but are not limited to, linear anhydrides of the structure RC(O)OC(O)R where R is independently H, liner, branched, or cyclic alkyl; liner, branched, or cyclic alkenyl; liner, branched, or cyclic alkynyl; aryl; liner, branched, or cyclic alkylaryl; liner, branched, or cyclic alkenylaryl; liner, branched, or cyclic alkynylaryl; N, O and/or S comprising heterocycle having one to four hetero atoms, where the carbons of R can be interrupted with one or more times with O, S, C(O), or C(O)NR" where R" is independently aryl, $C_1$ to $C_{10}$ alkyl, or $C_1$ to $C_{10}$ alkenyl, and where any of the carbon atoms of R can be substituted with a, $C_1$ to $C_{10}$ liner, branched, or cyclic alkyl, liner, branched, or cyclic alkenyl, liner, branched, or cyclic alkynyl, aryl, liner, branched, or cyclic alkylaryl, liner, branched, or cyclic alkenylaryl, liner, branched, or cyclic alkynylaryl, N, O and/or S comprising heterocycle having one to four hetero atoms, halogen, and alkoxy. The acid anhydride can be a cyclic anhydride such as, but not limited to succinic anhydride, glutaric anhydride, adipic anhydride, or pimelic anhydride. The alcohol employed for esterification with the anhydride can be, but is not limited to primary or secondary $C_1$ to $C_{30}$ alcohols of the structure $HOC(H)_xR_{3-x}$ where x is 1 to 3 and R is independently liner, branched, or cyclic alkyl; liner, branched, or cyclic alkenyl; liner, branched, or cyclic alkynyl; aryl; liner, branched, or cyclic alkylaryl; liner, branched, or cyclic alkenylaryl; liner, branched, or cyclic alkynylaryl; N, O and/or S comprising heterocycle having one to four hetero atoms, where the carbons of R can be interrupted with one or more times with O, S, C(O), NR", or C(O)NR", and where any of the carbon atoms of R can be substituted with a, $C_1$ to $C_{10}$ liner, branched, or cyclic alkyl, liner, branched, or cyclic alkenyl, liner, branched, or cyclic alkynyl, aryl, liner, branched, or cyclic alkylaryl, liner, branched, or cyclic alkenylaryl, liner, branched, or cyclic alkynylaryl, N, O and/or S comprising heterocycle having one or more hetero atoms, halogen, alkoxy, R"$_2$N where R" is independently aryl, $C_1$ to $C_{10}$ alkyl, or $C_1$ to $C_{10}$ alkenyl.

Figure 14:
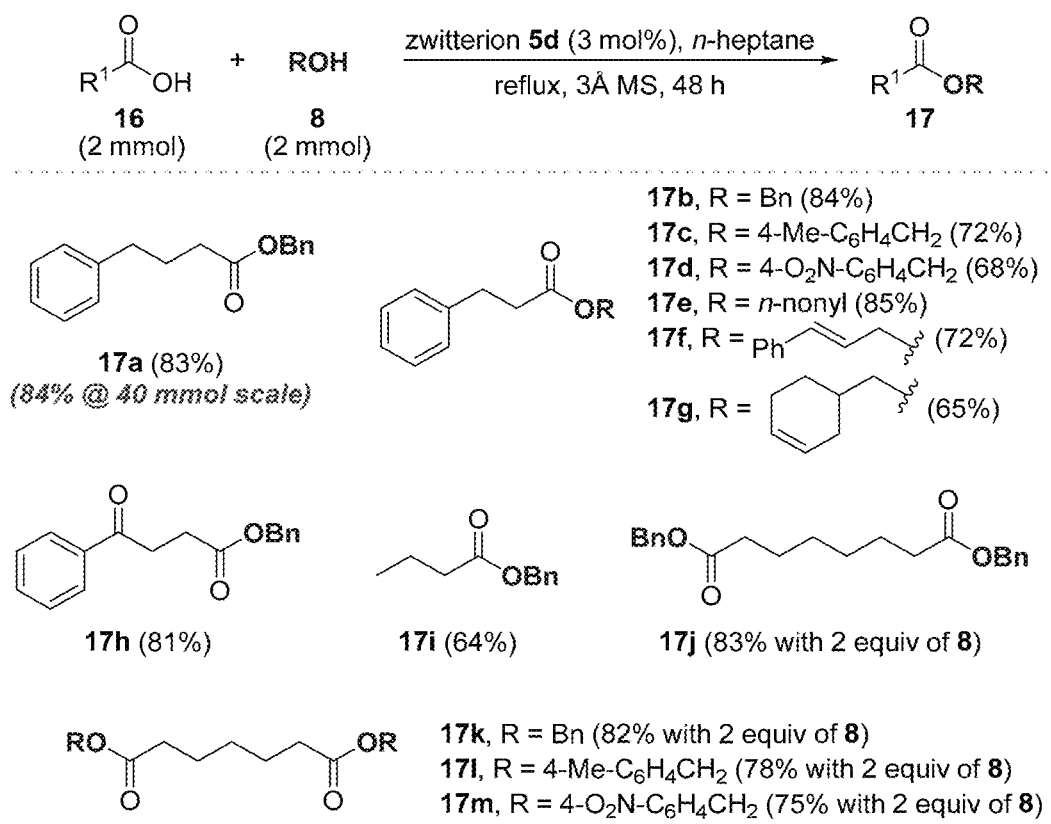
FIG. 14 shows reaction schemes for the esterification of various mono- and di-carboxylic acids wit benzyl alcohol employing the amide/iminium zwitterionic catalyst 5d, according to an embodiment of the invention.

The dehydrative esterification step of the anhydride esterification encourages catalyzing dehydrative esterification between a carboxylic acid and an alcohol, which is known to be challenging due to the high reaction barrier that requires strongly acidic catalysts to activate the carboxylic acid substrates. The sulfide/iminium zwitterion, 3b, was found to be ineffective in catalyzing the dehydrative esterification, attributed to alcoholysis of its constitutional component 3,5-(bistrifluoromethyl)phenyl isothiocyanate by benzyl alcohol. According to an embodiment of the invention, dehydrative esterification starting from carboxylic acids, for example, 16a-i of FIG. 14, and alcohols, such as benzyl alcohol 8a, yield the desired ester products, for example, 17a-i readably. Likewise, starting from diacids 16j-m, the corresponding diesters 17j-m are obtained in 75%-83% yields. The carboxylic acids can have, but are not limited to, the structure RC(O)OH where R is R is independently: H; liner, branched, or cyclic alkyl; liner, branched, or cyclic alkenyl; liner, branched, or cyclic alkynyl; aryl; liner, branched, or cyclic alkylaryl; liner, branched, or cyclic alkenylaryl; liner, branched, or cyclic alkynylaryl; or N, O and/or S comprising heterocycle having one to four hetero atoms, where the carbons of R is optionally interrupted with one or more times with O, S, C(O), or C(O)NR" where R" is independently aryl, $C_1$ to $C_{10}$ alkyl, or $C_1$ to $C_{10}$ alkenyl, and where any of the carbon atoms of R can be substituted with halogen, $C_1$ to $C_{10}$ liner, branched, or cyclic alkoxy, $C_1$ to $C_{10}$ liner, branched, or cyclic alkyl, liner, branched, or cyclic alkenyl, liner, branched, or cyclic alkynyl, aryl, liner, branched, or cyclic alkylaryl, liner, branched, or cyclic alkenylaryl, liner, branched, or cyclic alkynylaryl, N, O and/or S comprising heterocycle having one to four hetero atoms. The alcohol employed for esterification with the acid can be, but is not limited to primary or secondary $C_1$ to $C_{30}$ alcohols of the structure $HOC(H)_xR_{3-x}$ where x is 1 to 3 and R is independently liner, branched, or cyclic alkyl; liner, branched, or cyclic alkenyl; liner, branched, or cyclic alkynyl; aryl; liner, branched, or cyclic alkylaryl; liner, branched, or cyclic alkenylaryl; liner, branched, or cyclic alkynylaryl; N, O and/or S comprising heterocycle having one to four hetero atoms, where the carbons of R can be interrupted with one or more times with O, S, C(O), NR", or C(O)NR", and where any of the carbon atoms of R can be substituted with a, $C_1$ to $C_{10}$ liner, branched, or cyclic alkyl, liner, branched, or cyclic alkenyl, liner, branched, or cyclic alkynyl, aryl, liner, branched, or cyclic alkylaryl, liner, branched, or cyclic alkenylaryl, liner, branched, or cyclic alkynylaryl, N, O and/or S comprising heterocycle having one or more hetero atoms, halogen, alkoxy, R"$_2$N where R" is independently aryl, $C_1$ to $C_{10}$ alkyl, or $C_1$ to $C_{10}$ alkenyl.

Figure 15:
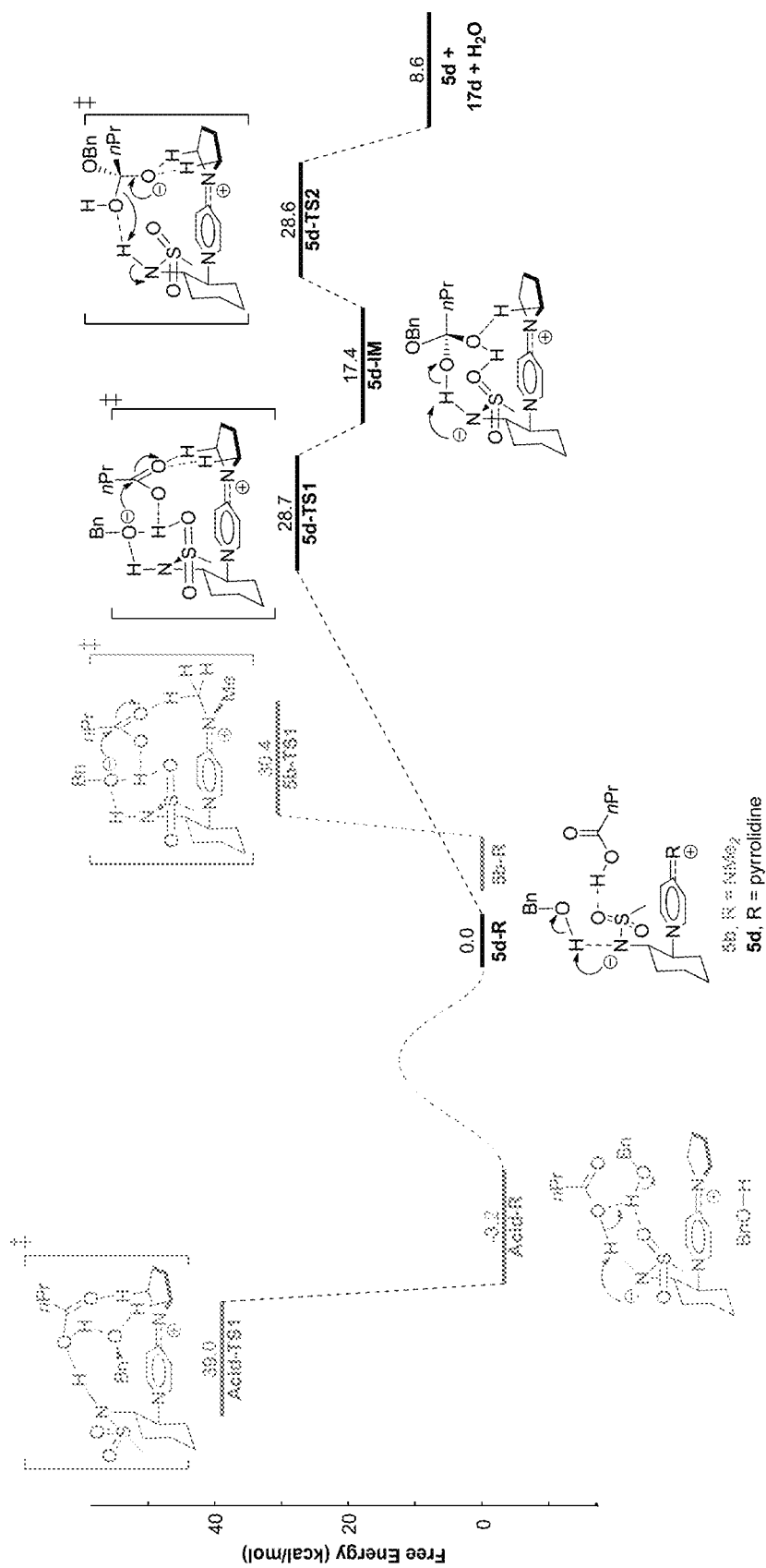
FIG. 15 shows a diagram for the calculated free energy profile consistent with a plausible mechanism for the dehydrative esterification using the amide/iminium zwitterionic catalyst, according to an embodiment of the invention.

The mechanism for the dehydrative esterification is particularly remarkable in that the reaction employs a non-acidic catalyst. $^1$H NMR experiments of benzyl alcohol 8a mixed with 5d and acetic acid mixed with 5d indicate that the alcohol and the carboxylic acid can interact with the zwitterion 5d. Density functional theory (DFT) calculations at the level of M06-2X (with Grimme D3)/6-311G(d,p) for the reaction between butyric acid (16i) and benzyl alcohol (8a) allow a better understanding on the reaction, as shown in FIG. 15, where two reaction pathways are considered: (1) the sulfonamide deprotonates the carboxylic acid; or (2) the sulfonamide deprotonates the alcohol. The calculations indicate, as shown in FIG. 15, that zwitterion 5d interacts with carboxylic acid 16i to form intermediate Acid-R, which is more stable than the adduct 5d-R (formed by the deprotonation of 8a by zwitterion 5d) by 3.2 kcal/mol. However, the subsequent step of nucleophilic attack of the carbonyl carbon by the alcohol (Acid-TS1) is highly disfavored because of the high free energy barrier ($\Delta G^{\ddagger}$=42.2 kcal/mol). The geometry optimization is consistent with the zwitterion/alcohol adduct 5d-R undergoing nucleophilic substitution at the carbonyl carbon to give the ortho-ester intermediate 5d-IM through 5d-TS1, with a significantly smaller free energy barrier ($\Delta G^{\ddagger}$=28.7 kcal/mol). As predicted by the Eyring equation, the rate constant associated with this small barrier is about $10^8$ times larger than that of the barrier of 42.2 kcal/mol in Acid-TS1. The interconversion barrier between Acid-R and 5d-R is likely to be significantly smaller than the energy barriers of 42.2 kcal/mol and 28.7 kcal/mol. Therefore, Acid-R appears to be a trap in the catalytic cycle, and the reaction likely proceeds to the final product via the rate-determining step 5d-R→5d-TS1. Subsequent collapse of the orthoester 5d-IM through 5d-TS2 gives the ester product 17i and water together with the regeneration of the zwitterionic catalyst 5d. Continuous removal of the water by-product from the reaction system favors the product formation.

Figure 16:
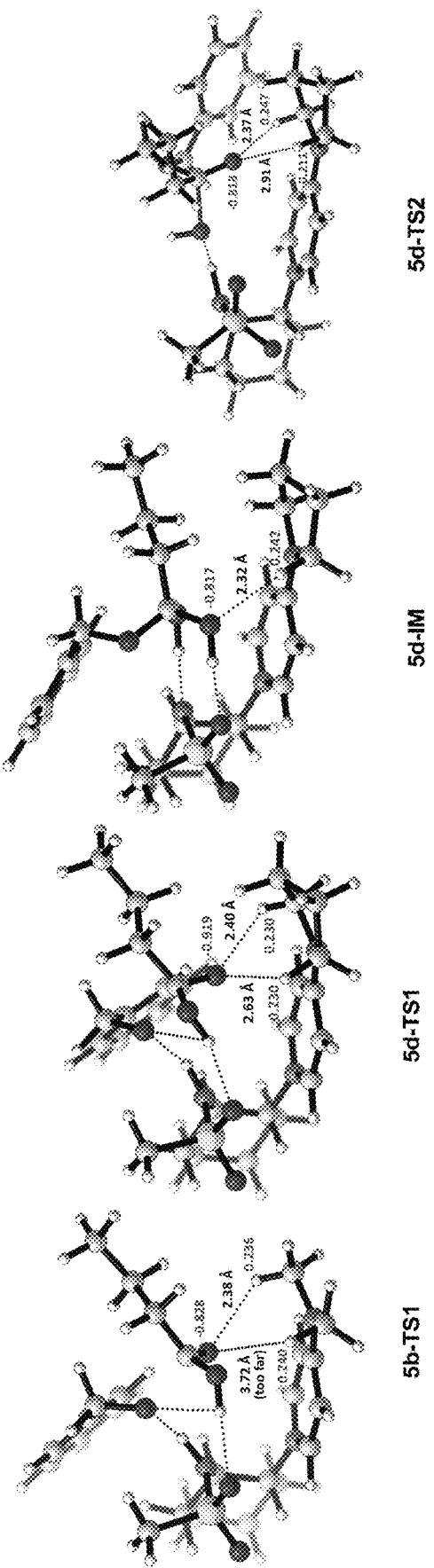
FIG. 16 shows calculated geometric structures for intermediates and transitions states for the reaction profile of FIG. 15 with distances between interacting atoms in angstrom and nitrogen and oxygen NBO atomic charges on atoms of the catalyst and acid.

In the optimized geometry of 5d-TS1, the pyrrolidine protons adjacent to the iminium cation in zwitterion 5d are positioned in close proximity to the oxygen of the carbonyl of 16i with distances at 2.40 and 2.63 Å (average=2.51 Å) as shown in FIG. 16. These values are within the range of a typical hydrogen bond interaction. Thus, a non-classical hydrogen bond appears to stabilize the intermediate and reduce the energy barrier. This result is consistent with the NMR study where the pyrrolidine's proton signals shifted up-field upon the addition of alcohol, potentially due to the interaction of the alkoxide anion with the pyrrolidine's protons through the non-classical hydrogen bonds. The system with the DMAP-derived catalyst 5b was also analyzed by DFT. The reaction encounters a considerably higher barrier ($\Delta G^\ddagger$=30.4 kcal/mol) at the rate-determining step 5b-TS1 as compared with 5d-TS1. The difference may be due to the restricted conformation available to the pyrrolidine's protons in 5d is due to the rigid PPY moiety, resulting in a greater stabilization of the carboxylic acid than is possible for the conformationally freely rotating methyl groups in the DMAP moiety of zwitterion 5b rendering the methyl groups less effective at stabilizing the transition state TS1 through non-classical hydrogen bonds. The closest distances between the carbonyl oxygen and the methyl protons in 5b-TS1 were calculated to be 3.72 Å and 2.38 Å(average=3.05 Å), which on average is considerably longer than that in 5d-TS1. These computational studies reveal the cooperative nature of the charge pair in zwitterion 5d in the dehydrative esterification.

Figure 17:
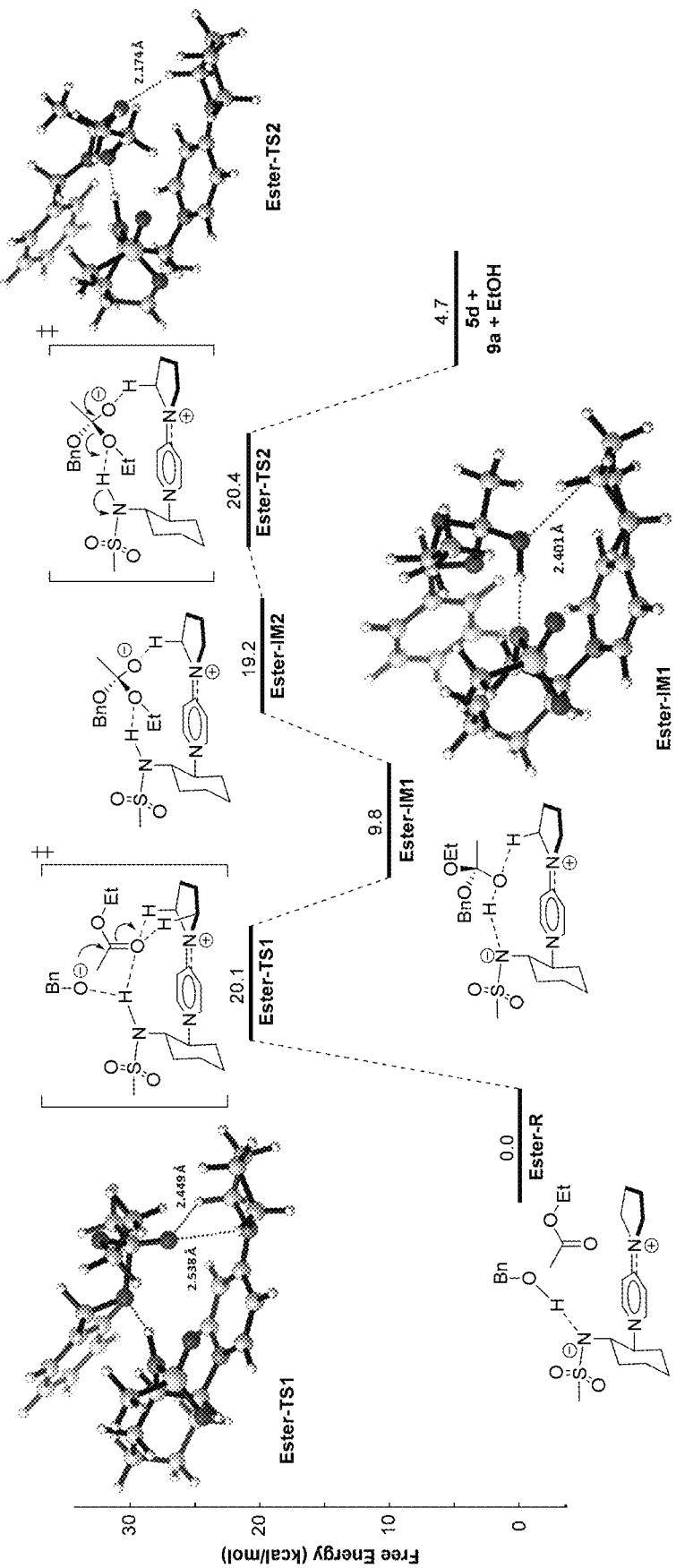
FIG. 17 shows a diagram for the calculated free energy profile consistent with a plausible mechanism for the transesterification mechanism overlaid with calculated geometric structures for intermediates and transitions states for the reaction profile.

DFT calculations for the transesterification reaction between benzyl alcohol (8a) and ethyl acetate with zwitterionic catalyst 5d are graphically represented in FIG. 17. A stable complex Ester-R originates from the hydrogen bond interaction between 5d and 8a, which is consistent with the NMR results. Based on the optimized energy profile, 8a attacks the ester through Ester-TS1 to give the tetrahedral intermediate Ester-IM1, which is stabilized by 7.2 kcal/mol. Similar to the case of dehydrative esterification, the carbonyl group of ethyl acetate is activated by the non-classical hydrogen bond originated from the pyrrolidine's protons (Ester-TS1, average distance of the O—H=2.493 Å). The step Ester-R→Ester-TS1 is the rate-determining step ($\Delta G^\ddagger$=21.2 kcal/mol). Re-organization of the complex (Ester-IM1→Ester-IM2) followed by collapse of the tetrahedral intermediate through Ester-TS2 gives the transesterification product, benzyl acetate (9a).

Although the zwitterion is not Brønsted acidic, the non-classical hydrogen bond in 5d appears to play an important role in activating the carbonyl group of carboxylic acid and ester in the dehydrative esterification and transesterification, respectively. A suitable catalyst pocket size defined by the distance between the anion and the cation in the zwitterionic system appears to be crucial in accommodating the reaction partners for high catalytic performance.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto. All publications referred to or cited herein are incorporated by reference in their entirety, including all figures and tables, to the extent they are not inconsistent with the explicit teachings of this specification.

The invention claimed is:

1. An amide/iminium zwitterionic catalyst, comprising a sulfonamide negative site and an iminium positive site with three to seven bonds residing between the sulfonamide negative site and the iminium positive site.

2. The amide/iminium zwitterionic catalyst according to claim 1, wherein the iminium is derived from a 4-aminopyridine, N-alkyl pyrrolidone, or an N-alkyl imidazole.

3. The amide/iminium zwitterionic catalyst according to claim 1, wherein the structure is:

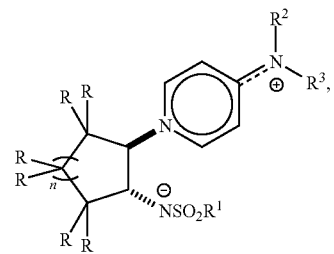

where: n is 1, 2, 3, or 4; R is independently H, aryl, $C_1$ to $C_6$ alkyl substituted aryl, $C_1$ to $C_6$ alkyl, aryl substituted $C_1$ to $C_6$ alkyl, wherein any of the carbons of the alky or aryl groups is unsubstituted or substituted with a $C_1$ to $C_6$ alkyl ether, aryl ether, $C_1$ to $C_6$ alkyl thioether, aryl thioether and where the alkyl is straight, branched, or cyclo alkyl, and where the alkyl is optionally interrupted one or more times with an O or S; $R^1$ is aryl, nitro substituted aryl, $C_1$ to $C_6$ alkyl substituted aryl, $C_1$ to $C_6$ alkyl, or $C_1$ to $C_6$ perfluoroalkyl; and $R^2$ and $R^3$ are independently $C_1$ to $C_6$ alkyl or in combination form a 5- or 6-membered ring heterocyclic ring, where the ring is optionally interrupted with one or more O, N, or NR' units, where R' is aryl, $C_1$ to $C_6$ alkyl substituted aryl, or $C_1$ to $C_6$ alkyl.

4. The amide/iminium zwitterionic catalyst according to claim 1, wherein the structure is:

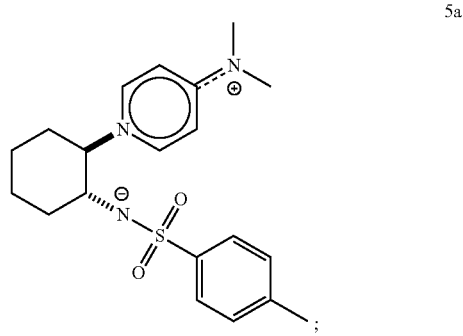

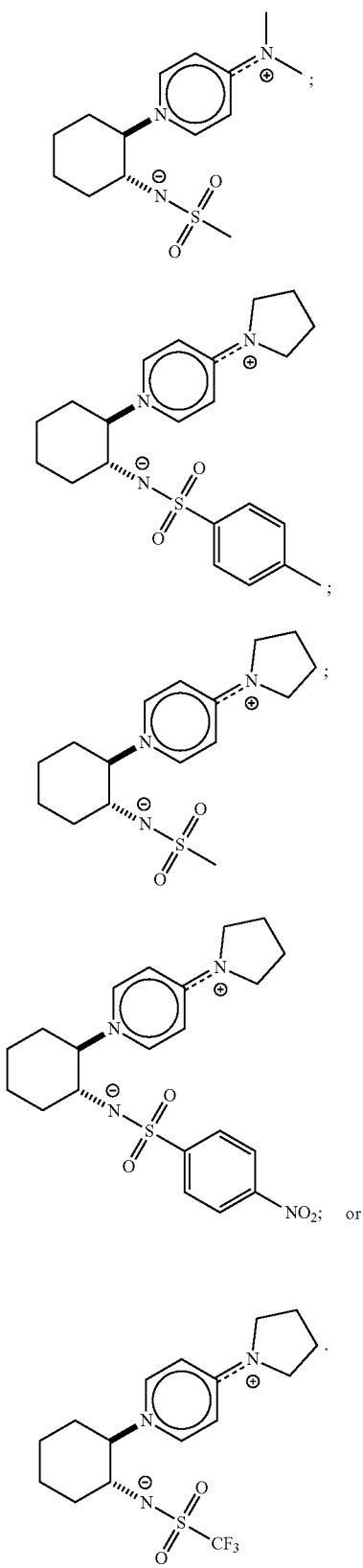

5. The amide/iminium zwitterionic catalyst according to claim 1, wherein the structure is:

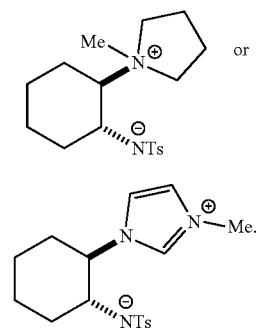

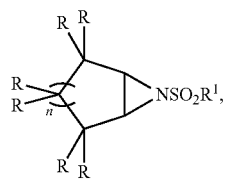

6. A method of forming an amide/iminium zwitterionic catalyst according to claim 1, comprising:
providing an N-sulfonated aziridine;
providing a nitrogen comprising heterocycle;
combine the N-sulfonated aziridine and the heterocycle; and
isolate the amide/iminium zwitterionic catalyst.

7. The method according to claim 6, wherein the N-sulfonated aziridine is an N-sulfonated cycloalkyl aziridine.

8. The method according to claim 6, wherein the N-sulfonated aziridine is:

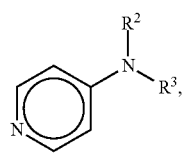

where: n is 1, 2, 3, or 4; R is independently H, aryl, $C_1$ to $C_6$ alkyl substituted aryl, $C_1$ to $C_6$ alkyl, aryl substituted $C_1$ to $C_6$ alkyl, wherein any of the carbons of the alky or aryl groups is unsubstituted or substituted with a $C_1$ to $C_6$ alkyl ether, aryl ether, $C_1$ to $C_6$ alkyl thioether, aryl thioether and where the alkyl is straight, branched, or cyclo alkyl, and where the alkyl is optionally interrupted one or more times with an O or S; and $R^1$ is aryl, nitro substituted aryl, $C_1$ to $C_6$ alkyl substituted aryl, $C_1$ to $C_6$ alkyl, or C to $C_6$ perfluoroalkyl.

9. The method according to claim 6, wherein the N-sulfonated aziridine is mesyl cyclohexene imine or tosyl cyclohexene imine.

10. The method according to claim 6, wherein the nitrogen comprising heterocycle is an N-alkyl pyrrolidone, an N-alkyl imidazole, a 4-(N,N-dialkylamino)pyridine, or a 4-pyrrolidylpyridine.

11. The method according to claim 6, wherein the nitrogen comprising heterocycle is:

where $R^2$ and $R^3$ are independently $C_1$ to $C_6$ alkyl or in combination form a 5- or 6-membered ring heterocyclic ring, where the ring is optionally interrupted with one or more O, N, or NR' units, where R' is aryl, $C_1$ to $C_6$ alkyl substituted aryl, or $C_1$ to $C_6$ alkyl.

12. An esterification method, comprising:
providing a amide/iminium zwitterionic catalyst according to claim 1;
providing a molecule comprising a carboxylic acid or a carboxylic acid derivative;
providing a molecule comprising an alcohol;
combining the molecule comprising a carboxylic acid or the molecule comprising a carboxylic acid derivative, the molecule comprising an alcohol, and the amide/iminium zwitterionic catalyst; and
isolating a molecule comprising an ester.

13. The esterification method according to claim 12, wherein the amide/iminium zwitterionic catalyst is wherein the iminium is derived from a 4-aminopyridine, N-alkyl pyrrolidone, or an N-alkyl imidazole.

14. The esterification method according to claim 12, wherein the amide/iminium zwitterionic catalyst is:

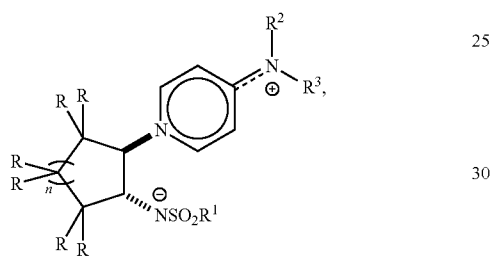

where: n is 1, 2, 3, or 4; R is independently H, aryl, $C_1$ to $C_6$ alkyl substituted aryl, $C_1$ to $C_6$ alkyl, aryl substituted $C_1$ to $C_6$ alkyl, wherein any of the carbons of the alky or aryl groups is unsubstituted or substituted with a $C_1$ to $C_6$ alkyl ether, aryl ether, $C_1$ to $C_6$ alkyl thioether, aryl thioether and where the alkyl is straight, branched, or cyclo alkyl, and where the alkyl is optionally interrupted one or more times with an O or S; $R^1$ is aryl, nitro substituted aryl, $C_1$ to $C_6$ alkyl substituted aryl, $C_1$ to $C_6$ alkyl, or $C_1$ to $C_6$ perfluoroalkyl; and $R^2$ and $R^3$ are independently $C_1$ to $C_6$ alkyl or in combination form a 5- or 6-membered ring heterocyclic ring, where the ring is optionally interrupted with one or more O, N, or NR' units, where R' is aryl, $C_1$ to $C_6$ alkyl substituted aryl, or $C_1$ to $C_6$ alkyl.

15. The esterification method according to claim 12, wherein the amide/iminium zwitterionic catalyst is:

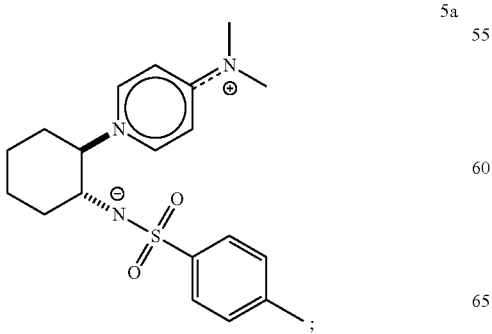

5a

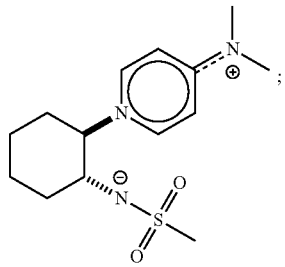

5b

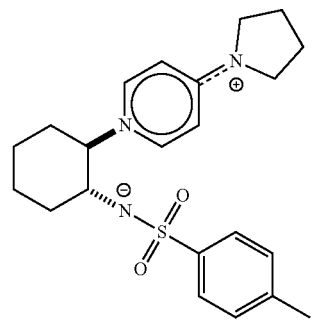

5c

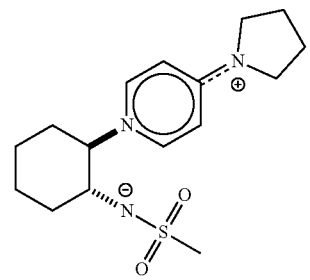

5d

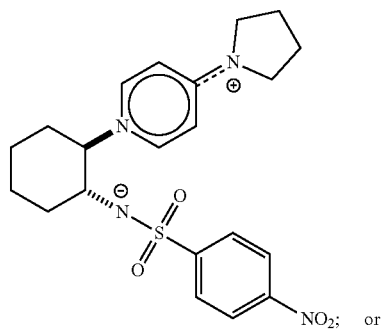

5e

NO₂; or

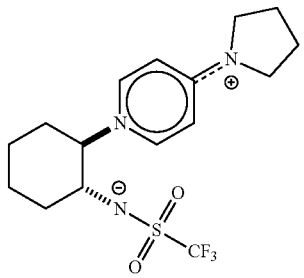

5f

16. The esterification method according to claim 12, wherein the molecule comprising an alcohol is a $C_1$ to $C_{30}$ alcohol of the structure $HOC(H)_xR_{3-x}$ where x is 1 to 3 and R is independently liner, branched, or cyclic alkyl; liner, branched, or cyclic alkenyl; liner, branched, or cyclic alkynyl; aryl; liner, branched, or cyclic alkylaryl; liner, branched, or cyclic alkenylaryl; liner, branched, or cyclic alkynylaryl; N, O and/or S comprising heterocycle having one to four hetero atoms, where the carbons of R can be interrupted with one or more times with O, S, C(O), NR", or C(O)NR", and where any of the carbon atoms of R can be substituted with a, $C_1$ to $C_{10}$ liner, branched, or cyclic alkyl, liner, branched, or cyclic alkenyl, liner, branched, or cyclic alkynyl, aryl, liner, branched, or cyclic alkylaryl, liner, branched, or cyclic alkenylaryl, liner, branched, or cyclic alkynylaryl, N, O and/or S comprising heterocycle having one or more hetero atoms, halogen, alkoxy, $R"_2N$ where R" is independently aryl, $C_1$ to $C_{10}$ alkyl, or $C_1$ to $C_{10}$ alkenyl.

17. The esterification method according to claim 12, wherein the molecule comprising a carboxylic acid or a carboxylic acid derivative is a carboxylic acid is RC(O)OH where R is R is independently: H; liner, branched, or cyclic alkyl; liner, branched, or cyclic alkenyl; liner, branched, or cyclic alkynyl; aryl; liner, branched, or cyclic alkylaryl; liner, branched, or cyclic alkenylaryl; liner, branched, or cyclic alkynylaryl; or N, O and/or S comprising heterocycle having one to four hetero atoms, where the carbons of R is optionally interrupted with one or more times with O, S, C(O), or C(O)NR" where R" is independently aryl, $C_1$ to $C_{10}$ alkyl, or $C_1$ to $C_{10}$ alkenyl, and where any of the carbon atoms of R can be substituted with halogen, $C_1$ to $C_{10}$ liner, branched, or cyclic alkoxy, $C_1$ to $C_{10}$ liner, branched, or cyclic alkyl, liner, branched, or cyclic alkenyl, liner, branched, or cyclic alkynyl, aryl, liner, branched, or cyclic alkylaryl, liner, branched, or cyclic alkenylaryl, liner, branched, or cyclic alkynylaryl, N, O and/or S comprising heterocycle having one to four hetero atoms.

18. The esterification method according to claim 12, wherein the molecule comprising a carboxylic acid or a carboxylic acid derivative is a carboxylic ester of the structure RC(O)OR' where: R is selected from, but not limited to, H, liner, branched, or cyclic alkyl; liner, branched, or cyclic alkenyl; liner, branched, or cyclic alkynyl; aryl; liner, branched, or cyclic alkylaryl; liner, branched, or cyclic alkenylaryl; liner, branched, or cyclic alkynylaryl; N, O and/or S comprising heterocycle having one to four hetero atoms, where the carbons of R are optionally interrupted with one or more times with O, S, C(O), or C(O)NR" where R" is independently aryl, $C_1$ to $C_{10}$ alkyl, or $C_1$ to $C_{10}$ alkenyl, and where any of the carbon atoms of R can be substituted with a, $C_1$ to $C_{10}$ liner, branched, or cyclic alkyl, liner, branched, or cyclic alkenyl, liner, branched, or cyclic alkynyl, aryl, liner, branched, or cyclic alkylaryl, liner, branched, or cyclic alkenylaryl, liner, branched, or cyclic alkynylaryl, N, O and/or S comprising heterocycle having one to four hetero atoms, halogen, and alkoxy; and R' is selected from methyl, ethyl, n-propyl, i-propyl, n-butyl, i-butyl, sec-butyl, tert-butyl or neo-pentyl.

19. The esterification method according to claim 12, wherein the molecule comprising a carboxylic acid or a carboxylic acid derivative is a triglyceride of the structure:

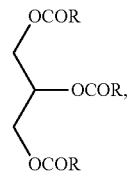

where R is independently a straight or branched $C_1$ to $C_{26}$ alkyl chain, straight or branched $C_3$ to $C_{26}$ alkenyl chain having 1 to 6 degrees of unsaturation.

20. The esterification method according to claim 12, wherein the molecule comprising a carboxylic acid or a carboxylic acid derivative is a carboxylic acid anhydride of the structure RC(O)OC(O)R where R is independently H, liner, branched, or cyclic alkyl; liner, branched, or cyclic alkenyl; liner, branched, or cyclic alkynyl; aryl; liner, branched, or cyclic alkylaryl; liner, branched, or cyclic alkenylaryl; liner, branched, or cyclic alkynylaryl; N, O and/or S comprising heterocycle having one to four hetero atoms, where the carbons of R id optionally interrupted with one or more times with O, S, C(O), or C(O)NR" where R" is independently aryl, $C_1$ to $C_{10}$ alkyl, or $C_1$ to $C_{10}$ alkenyl, and where any of the carbon atoms of R can be substituted with a, $C_1$ to $C_{10}$ liner, branched, or cyclic alkyl, liner, branched, or cyclic alkenyl, liner, branched, or cyclic alkynyl, aryl, liner, branched, or cyclic alkylaryl, liner, branched, or cyclic alkenylaryl, liner, branched, or cyclic alkynylaryl, N, O and/or S comprising heterocycle having one to four hetero atoms, halogen, or alkoxy.

21. The esterification method according to claim 12, wherein the molecule comprising a carboxylic acid or a carboxylic acid derivative is a triglyceride and the molecule comprising an ester is a fatty acid methyl ester (FAME).

22. The esterification method according to claim 21, wherein the FAME is the methyl ester of butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid; arachidic acid, heneicosylic acid, behenic acid, tricosylic acid, lignoceric acid, pentacosylic acid, cerotic acid, carboceric acid, montanic acid, nonacosylic acid, melissic acid, hentriacontylic acid, lacceroic acid, psyllic acid, geddic acid, ceroplastic acid, hexatriacontylic acid, heptatriacontylic acid, octatriacontylic acid, nonatriacontylic acid, tetracontylic acid, α-linolenic acid, stearidonic acid, eicosapentaenoic acid, docosahexaenoic acid, linoleic acid, linolelaidic acid, γ-linolenic acid, dihomo-γ-linolenic acid, arachidonic acid, docosatetraenoic acid, palmitoleic acid, vaccenic acid, paullinic acid, oleic acid, elaidic acid, gondoic acid, erucic acid, nervonic acid, mead acid, or any combination thereof.

23. The esterification method according to claim 12, wherein the molecule comprising a carboxylic acid or a carboxylic acid derivative and the molecule comprising an alcohol is combined as an alcohol substituted carboxylic ester of the structure $HO(CH_2)_xC(O)OR$ where x is 3-5 and R' is selected from methyl, ethyl, or propyl, wherein molecule comprising an ester is a lactone.

24. The esterification method according to claim 12, wherein the molecule comprising an ester is a fluoroindole-derivative.

* * * * *